United States Patent
Chadha et al.

(10) Patent No.: US 10,670,572 B2
(45) Date of Patent: Jun. 2, 2020

(54) WIRELESS EXPOSURE MONITOR

(71) Applicant: Applied Particle Technology, Inc., St. Louis, MO (US)

(72) Inventors: Tandeep Singh Chadha, Louisville, KY (US); Jiaxi Fang, Clayton, MO (US); Pratim Biswas, Chesterfield, MO (US)

(73) Assignee: Applied Particle Technology, Inc., St. Louis, MO (US)

( * ) Notice: Subject to any disclaimer, the term of this patent is extended or adjusted under 35 U.S.C. 154(b) by 0 days.

(21) Appl. No.: 16/293,499

(22) Filed: Mar. 5, 2019

(65) Prior Publication Data

US 2019/0277822 A1  Sep. 12, 2019

Related U.S. Application Data

(60) Provisional application No. 62/638,958, filed on Mar. 6, 2018.

(51) Int. Cl.
*G01N 33/00* (2006.01)
*G01N 15/06* (2006.01)
(Continued)

(52) U.S. Cl.
CPC ..... *G01N 33/0075* (2013.01); *G01N 15/0266* (2013.01); *G01N 15/0656* (2013.01); *G01N 33/0031* (2013.01); *G01N 33/0065* (2013.01)

(58) Field of Classification Search
CPC ........... G01N 15/0266; G01N 15/0656; G01N 33/0031; G01N 33/0065; G01N 33/0075
See application file for complete search history.

(56) References Cited

U.S. PATENT DOCUMENTS 7,389,158 B2 *  6/2008  Desrochers .............. G01N 1/26
                                                    700/276
8,190,367 B2 *  5/2012  Bassa ................. B60H 1/00771
                                                       702/3
(Continued)

FOREIGN PATENT DOCUMENTS

GB           2420616 A      5/2006

OTHER PUBLICATIONS

Applied Particle Technology, "Minima" brochure, 2017, 2 pp.
(Continued)

*Primary Examiner* — Sisay Yacob
(74) *Attorney, Agent, or Firm* — Weaver Austin Villeneuve & Sampson LLP

(57) ABSTRACT

Systems, apparatuses, and methods for monitoring an environment are provided. These systems, apparatus, and methods may include a monitoring unit positioned within the environment that includes an air quality sensor configured to generate particle data, a communications unit configured to directly or indirectly transmit data between the monitoring unit and a remote computing unit, and a controller with instructions to cause the air quality sensor to generate particle data about particles in the environment, and transmit the particle data to the remote computing unit. The remote computing unit may be positioned outside the environment, and include a second processor, another communications unit, and another non-transitory memory device with instructions to receive and store the particle data, and determine, based on the received particle data generated by the air quality sensor, whether a first exposure threshold has been exceeded for the monitoring unit.

76 Claims, 12 Drawing Sheets

(51) Int. Cl.
    *G01B 15/02*     (2006.01)
    *G01N 15/02*     (2006.01)

(56) References Cited

U.S. PATENT DOCUMENTS

| | | | | |
|---|---|---|---|---|
| 8,781,633 | B2* | 7/2014 | Fata | G05B 15/02 |
| | | | | 700/276 |
| 9,141,094 | B2 | 9/2015 | Pariseau et al. | |
| 2002/0144537 | A1* | 10/2002 | Sharp | G01N 1/26 |
| | | | | 73/31.01 |
| 2003/0016128 | A1 | 1/2003 | Lutz et al. | |
| 2006/0173580 | A1* | 8/2006 | Desrochers | G01N 1/26 |
| | | | | 700/276 |
| 2009/0265037 | A1* | 10/2009 | Bassa | B60H 1/00771 |
| | | | | 700/276 |
| 2010/0274366 | A1* | 10/2010 | Fata | G05B 15/02 |
| | | | | 700/7 |
| 2010/0295672 | A1 | 11/2010 | Hyland et al. | |
| 2013/0213115 | A1 | 8/2013 | Chu et al. | |
| 2014/0347663 | A1 | 11/2014 | Rodes et al. | |
| 2015/0212057 | A1 | 7/2015 | Darveau | |
| 2016/0109349 | A1 | 4/2016 | Volckens et al. | |
| 2016/0202224 | A1* | 7/2016 | Lloyd | G01N 33/0016 |
| | | | | 73/865.8 |
| 2017/0284690 | A1 | 10/2017 | Lipanov | |
| 2017/0370809 | A1 | 12/2017 | Miller-Lionberg et al. | |

OTHER PUBLICATIONS

International Search Report and Written Opinion dated Jun. 19, 2019 from PCT Application No. PCT/US2019/020811.

Li, J., et al., "Optical characterization studies of a low-cost particle sensor," Aerosol and Air Quality Research, 17: 2017, pp. 1691-1704. <doi: 10.4209/aaqr.2017.02.0085>.

Wang, Y., et al., "Laboratory evaluation and calibration of three low-cost particle sensors for particulate matter measurement," Aerosol Science and Technology, vol. 49, 2015, pp. 1063-1077. <doi: 10.1080/02786826.2015.1100710>.

Li, J., et al., "Spatiotemporal distribution of indoor particulate matter concentration with a low-cost sensor network," Building and Environment 127, 2018, pp. 138-147. <doi: 10.1016/j.buildenv.2017.11.001>.

Li, J., et al., "Robust algorithms & innovative designs for low cost PM sensors: calibration, characterization, and application," Air Sensors International Conference, Oakland, CA, Sep. 13, 2018, 20 pp.

* cited by examiner

WIRELESS EXPOSURE MONITOR

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

In many industries and environments, the potential exists that personnel, workers, and persons may be exposed to harmful conditions, such as aerosols, gases, volatile organic compounds (VOCs), temperature, humidity, and noise. It is desirable to detect the presence of harmful conditions and determine whether there has been any unsafe exposure to these conditions.

SUMMARY

In some embodiments, a system may be provided. The system may include a monitoring unit positioned within an environment and that includes an air quality sensor configured to generate particle data regarding particles in the environment, a first communications unit with an antenna configured to transmit data between the monitoring unit and, directly or indirectly, a remote computing unit, and a controller including one or more first processors and one or more first non-transitory memory devices that store instructions for controlling the one or more first processors to cause the air quality sensor to generate particle data about particles in the environment, and transmit, using the first communications unit, the particle data generated by the air quality sensor to the remote computing unit. In some embodiments, the remote computing unit may be positioned outside the environment and may contain one or more second processors, one or more second communications unit, and one or more second non-transitory memory devices that stores instructions for controlling the one or more second processors to receive and store the particle data, and determine, based on the received particle data generated by the air quality sensor, whether a first exposure threshold has been exceeded for the monitoring unit.

In some embodiments, the first communications unit and controller may be configured as a single unit.

In some embodiments, the monitoring unit may further includes a temperature sensor configured to generate temperature data, a pressure sensor configured to generate pressure data, and a relative humidity sensor configured to generate pressure data. The one or more first non-transitory memory devices of the monitoring unit may store further instructions for controlling the one or more first processors to cause the air temperature sensor to generate temperature data, cause the air pressure sensor to generate pressure data, cause the relative humidity sensor to generate humidity data, and transmit, using the first communications unit, the temperature data, pressure data, and humidity data to the remote computing unit. The one or more second non-transitory memory devices of the remote computing unit may store further instructions for controlling the one or more second processors to receive and store the temperature data, the pressure data, and the humidity data, determine, based on the received particle data, temperature data, pressure data, and the humidity data, first adjusted particle information, and determine, based on the first adjusted particle information, whether the first exposure threshold has been exceeded.

In some embodiments, the system may further include a notification mechanism configured to present a person with a notification related to the particle data. The one or more second non-transitory memory devices of the remote computing unit may store further instructions for controlling the one or more second processors to cause, based on the particle data, the notification mechanism to present the person with the notification related to the particle data.

In some embodiments, the one or more second non-transitory memory devices of the remote computing unit may further stores environmental data about the environment. The one or more second non-transitory memory devices of the remote computing unit stores further instructions for controlling the one or more second processors to access the environmental data, determine, based on the received particle data and the environmental data, second adjusted particle information, and determine, based on the second adjusted particle information, whether the first exposure threshold has been exceeded.

In some such embodiments, the environmental data may include one or more of: material safety data sheet (MSDS) data, weather data, historical detected particle data, data generated by another monitoring unit in the environment, data regarding activity being performed in the environment, and public data.

In some embodiments, the system may further include a second monitoring unit positioned within the environment and that may include a second air quality sensor configured to generate data regarding particles in the environment, a third communications unit with an antenna configured to transmit data between the second monitoring unit and the remote computing unit, and a second controller comprising one or more third processors and one or more third non-transitory memory devices that store instructions for controlling the one or more third processors to cause the second air quality sensor to generate second particle data about particles in the environment, and transmit, using the third communications unit, the second particle data generated by the air quality sensor to the remote computing unit. The first communications unit may be further configured to transmit data between the second monitoring unit, and the one or more second non-transitory memory devices of the remote computing unit may store further instructions for controlling the one or more second processors to receive and store the second particle data, and determine, based on the received second particle data, whether the first exposure threshold has been exceeded for the second monitoring unit.

In some such embodiments, the one or more second non-transitory memory devices of the remote computing unit may store further instructions for controlling the one or more second processors to determine, based on the received particle data and the second particle data, whether the particle data is offset from the second particle data by a first offset.

In some such embodiments, the monitoring unit may be a mobile monitoring unit configured to be moved within the environment, and the second monitoring unit may be a stationary monitory unit in a fixed position within the environment.

In some such embodiments, the monitoring unit and the second monitoring unit may be mobile monitoring units configured to be moved within the environment.

In some embodiments, the first exposure threshold may include a time-weighted average, an acute exposure limit, an upper exposure limit, a lower exposure limit, a combustible limit, and a short-term exposure limit.

In some embodiments, the monitoring unit may further include an accelerometer, a gyroscope, and a microphone, and the one or more first non-transitory memory devices stores further instructions for controlling the one or more first processors to cause the accelerometer to generate accelerometer data, the gyroscope to generate gyroscopic data, and the microphone to generate sound data, and transmit, using the first communications unit, the accelerometer data, gyroscopic data, and sound data, to the remote computing unit. The one or more second non-transitory memory devices may store further instructions for controlling the one or more second processors to determine, based on the accelerometer data, gyroscopic data, and sound data, an activity being performed within a first distance from the monitoring unit.

In some such embodiments, the one or more second non-transitory memory devices may store further instructions for controlling the one or more second processors to determine, based on the accelerometer data, gyroscopic data, and sound data, whether a wearer of the monitoring unit is performing an activity.

In some embodiments, the one or more second non-transitory memory devices of the remote computing unit may store further instructions for controlling the one or more second processors to determine, based on the received particle data and the second particle data, whether the first exposure threshold has been exceeded for the monitoring unit.

In some embodiments, a monitoring unit may be provided. The monitoring unit may include a case with an inlet and an outlet, an air quality sensor fluidically connected to the inlet and the outlet, and configured to generate particle data regarding particles in air drawn through the inlet, a communications unit with an antenna configured to transmit data between the monitoring unit and a remote computing unit, and a controller that may include one or more processors and one or more non-transitory memory devices. The case may encompass the air quality sensor, the communications unit, and the controller, and the one or more non-transitory memory devices may store instructions for controlling the one or more processors to cause the air quality sensor to generate particle data about particles in air drawn through the inlet, and transmit, using the communications unit, the data generated by the air quality sensor to the remote computing unit.

In some embodiments, the monitoring unit may further include a notification mechanism configured to present a person with a notification related to the particle data, and the one or more non-transitory memory devices may store further instructions for controlling the one or more processors to cause, based on the particle data, the notification mechanism to present the person with the notification related to the particle data.

In some such embodiments, the notification mechanism may include a display on the case that is configured to present the notification to the person.

In some such embodiments, the one or more non-transitory memory devices may store further instructions for controlling the one or more processors to receive a remote instruction from the remote computing unit, and cause, based on the remote instruction received from the remote computing unit, the notification mechanism to present the person with the notification related to the particle data.

In some such embodiments, the notification may be one or more of alarm, alert, message, an auditory output, an electronic communication, an electromagnetic communication, a visual output, and a tactile output.

In some embodiments, the monitoring unit may further include a temperature sensor, a pressure sensor, and a relative humidity sensor. The one or more non-transitory memory devices may store further instructions for controlling the one or more processors to cause the air temperature sensor to generate temperature data, cause the air pressure sensor to generate pressure data, cause the relative humidity sensor to generate humidity data, and transmit, using the communications unit, the temperature data, pressure data, and humidity data to the remote computing unit.

In some embodiments, the monitoring unit may further include an accelerometer, a gyroscope, a microphone, and a camera. The one or more non-transitory memory devices may store further instructions for controlling the one or more processors to cause the accelerometer to generate accelerometer data, cause the gyroscope sensor to generate gyroscopic data, cause the microphone to generate sound data, cause the camera to generate imaging data, and transmit, using the communications unit, the accelerometer data, gyroscopic data, sound data, and imaging data to the remote computing unit.

In some embodiments, the communications unit may be further configured to gather position data about a position of the monitoring unit within an environment, and the one or more non-transitory memory devices may store further instructions for controlling the one or more processors to cause the communications unit is further configured to gather position data about the position of the monitoring unit within an environment, and transmit the position data to the remote computing unit.

In some embodiments, the monitoring unit may further include a second air quality sensor fluidically connected to the inlet and the outlet, and configured to generate second particle data regarding particles in air drawn through the inlet. The one or more non-transitory memory devices may store further instructions for controlling the one or more processors to cause the second air quality sensor to generate second particle data about particles in air drawn through the inlet, determine, based on the particle data and the second particle data, whether the particle data is offset from the second particle data by a first offset, and transmit information related to the determination of the first offset to the remote computing unit.

In some embodiments, the monitoring unit may further include wearable features that are configured to enable the monitoring unit to be worn by a person within that person's breathing zone.

In some embodiments, another monitoring unit may be provided. The other monitoring unit may include a case with an inlet and an outlet, an air quality sensor fluidically connected to the inlet and the outlet, and configured to generate data regarding particles in air drawn through the inlet, a communications unit with an antenna configured to transmit data between the monitoring unit and a remote computing unit, a temperature sensor configured to generate temperature data, a pressure sensor configured to generate pressure data, a relative humidity sensor configured to generate humidity data, an accelerometer configured to generate accelerometer data, a gyroscope configured to generate gyroscopic data, a microphone configured to generate sound data, a camera configured to generate imaging data, and a controller comprising one or more processors and one or more non-transitory memory devices.

In some embodiments, a method for monitoring conditions of an environment may be provided. The method may include generating, using an air quality sensor on a monitoring unit positioned within the environment, particle data regarding particles in the environment, transmitting the particle data from the monitoring unit to a remote computing unit outside the environment, and determining, based on the particle data generated by the air quality sensor, whether a first threshold has been exceeded.

In some embodiments, the transmitting may be performed simultaneously with the generating.

In some embodiments, the determining may be at least partially performed on the remote computing unit.

In some embodiments, the method may further include generating, using a temperature sensor, a pressure sensor, and a relative humidity sensor on the monitoring unit, temperature data, pressure data, and humidity data, respectively, transmitting the temperature data, pressure data, and humidity data from the monitoring unit to the remote computing unit, determining, based on the particle data, temperature data, pressure data, and humidity data, adjusted particle information, and determining, based on the adjusted particle information, and whether the first threshold has been exceeded.

In some embodiments, the method may further include generating, using an accelerometer, a gyroscope, and a microphone on the monitoring unit, accelerometer data, gyroscopic data, and sound data, respectively, transmitting the accelerometer data, gyroscopic data, and sound data from the monitoring unit to the remote computing unit, and determining, based on accelerometer data, gyroscopic data, and sound data, whether an activity is being performed within a first distance of the monitoring unit.

In some such embodiments, the method may further include determining, based on accelerometer data, gyroscopic data, and sound data, whether the activity is being performed by a wearer of the monitoring unit.

In some such embodiments, the method may further include generating, based on one or more of accelerometer data, gyroscopic data, and sound data, imaging data using a camera on the monitoring unit, and transmitting the imaging data from the monitoring unit to the remote computing unit.

In some embodiments, an apparatus for monitoring one or more environmental parameters including aerosol properties, gas concentrations, temperature, humidity or noise may be provided. The apparatus may be capable of wirelessly transmitting data generated by one or more sensors and may include (a) one or more sensor(s) for generating data corresponding to one or more environmental parameters such as aerosol properties, gas concentrations, temperature, humidity or noise, (b) a microprocessor/microcontroller to read the data and transmit wirelessly, (c) a screen to display the data, (d) an optional memory card to store the data, (e) a cloud server for receiving the data, applying, algorithms and displaying the data, and (f) an optional imaging device to take the image/record video while the data is being recorded.

In some embodiments, the data corresponding to measured aerosol properties may include one or more of particle mass concentrations (PM0.5, PM1, PM2.5, PM4, PM5, PM10), the particle number counts in different size bins, particle refractive index, fractal dimension, chemical composition, and other material properties.

In some embodiments, the apparatus may be placed on a person in the breathing zone to monitor personal exposure.

In some embodiments, the apparatus may be placed at different locations at an industrial site.

In some embodiments, the apparatus may be used to prevent exposure to a person above the action levels and permissible exposure limits as defined by NIOSH/OSHA.

In some embodiments, real-time alerts may be generated based on the data.

In some embodiments, the data may be transmitted wirelessly via WiFi, Bluetooth, cellular or LoRAwan.

In some embodiments, the apparatus may further include a camera that may be configured and placed to take images/record video while the monitor is running.

In some such embodiments, the camera may take an image or records video when an aspect of the data goes above a certain level.

In some embodiments, the apparatus may be used as a wearable exposure monitor for occupational safety and health applications.

In some embodiments, the apparatus may be used as an industrial site monitor.

In some embodiments, data from a network of monitors may be taken to create a map of air quality in real-time.

In some embodiments, the data is used to calculate the concentrations of certain elements/compounds including but not limited to silica, hexavalent chromium, and lead.

In some embodiments, the data may be used for process control for emission sources.

These and other features of the disclosure will be discussed in more detail below with reference to the drawings.

BRIEF DESCRIPTION OF THE DRAWINGS

The various implementations disclosed herein are illustrated by way of example, and not by way of limitation, in the figures of the accompanying drawings, in which like reference numerals refer to similar elements.

DETAILED DESCRIPTION

Figure 1:
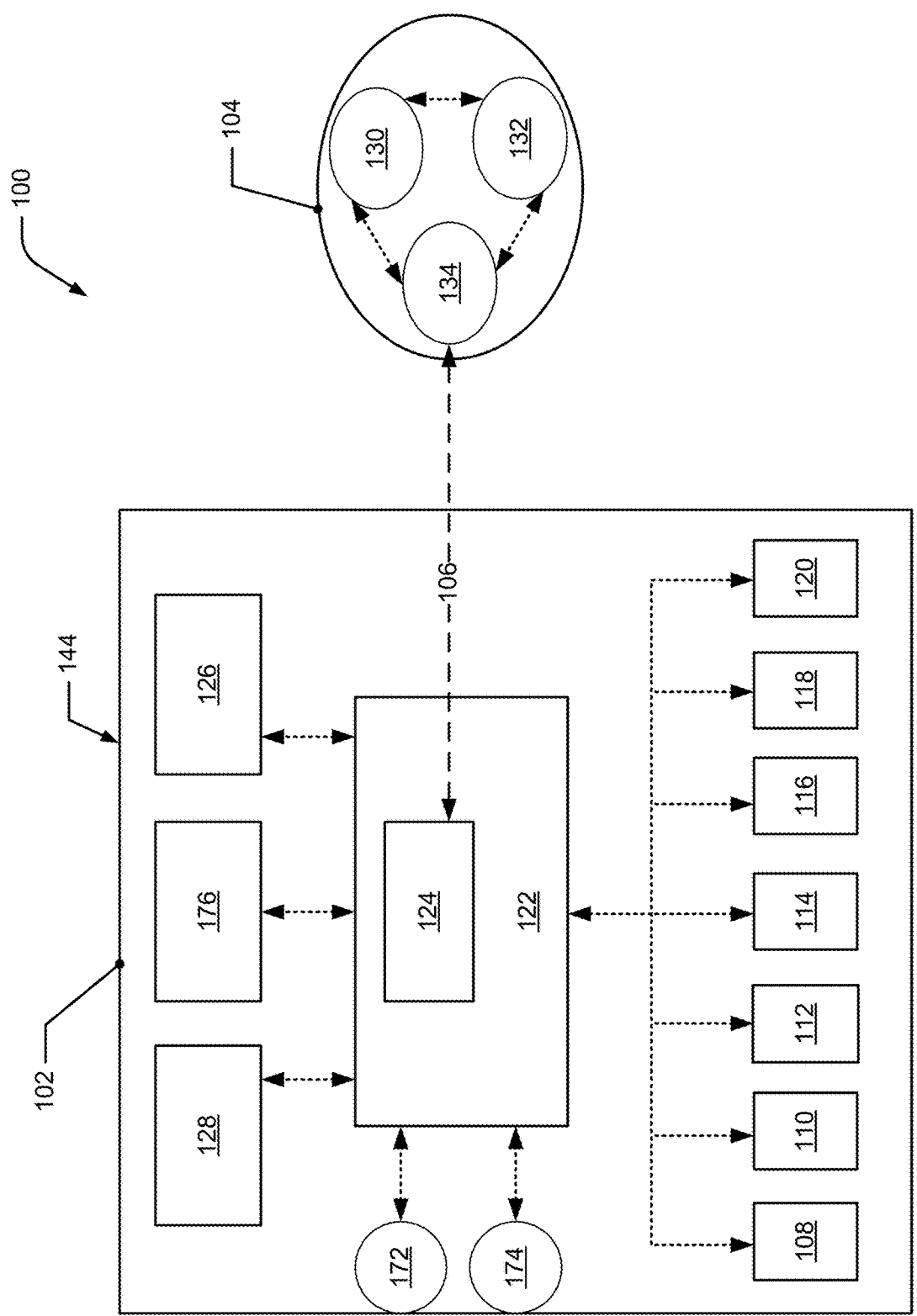
FIG. 1 depicts a first example system for monitoring environmental conditions.

In the following description, certain details are set forth in order to assist understanding the presented embodiments. The disclosed embodiments may be practiced without some or all of these details. Thus, while the disclosed embodiments will be described in conjunction with the certain details, it should be understood that these are not intended to limit the disclosed embodiments. Further, in some instances, well-known process operations have not been described in detail to clarify the disclosed embodiments.

Definitions

"Cloud computing" uses one or more servers, data stores, or other computational resources that are hosted remotely, i.e., not on an end user's desktop or laptop computer, handheld computational device, or other device directly accessible to the user. Cloud-based computational resources are generally accessible via a network such as the internet. Cloud-based resources may store, manage, and process data. Frequently, the resources are shared software and/or hardware. Cloud-based computational resources provide information, storage, and/or processing resources to computers and other devices upon request. Access to cloud resources may be by wired or wireless communication.

"Edge computing" uses one or more servers, data stores, or other computational resources that are hosted on site, locally, using a similar infrastructure as in cloud computing. As an example, edge computing may be performed using private networks where the user might not want data to go to the internet.

"Mobile Monitoring Unit" as used herein means a monitoring device that is not at a fixed location while monitoring. Typically, a mobile monitoring device moves about while monitoring. As examples, a mobile monitoring device may be worn by a user (it is wearable), be positioned on a flying device such as a drone, or positioned on a terrestrial vehicle.

"Sensor" as used herein means any device capable of detecting and/or measuring a physical property. Examples include a particle sizer, an air quality monitor, a specific matter sensor, a temperature sensor (e.g., thermocouple, resistance temperature detector, negative temperature coefficient thermistor), a relative humidity sensor (e.g., capacitive, resistive, thermally conductive), a pressure sensor (e.g., a piezometer, a manometer, etc.), a microphone (e.g., a dynamic, condenser, piezoelectric, carbon, ribbon), an inertial sensor (e.g., an accelerometer and/or gyroscope), and a gas sensor (e.g., a sensor configured to detect one orm or more specific gases such as carbon monoxide (CO), carbon dioxide ($CO_2$), Ozone, nitrogen oxides (NOx), volatile organic compounds (VOCs), hydrogen cyanide (HCN). Sensors may employ any of various transduction mechanisms including mechanical (including electromecahnical), optical, chemical, biomimetic, and electrical.

"Stationary Monitoring Unit" as used herein means a monitoring unit that is positioned in a fixed location. In certain embodiments, a stationary monitoring unit is used in conjunction with a mobile monitoring unit. A stationary unit may be affixed to an immobile object, such as a wall, building, fence, pole, structural frame, piece of equipment (e.g., a generator). In some implementations, the stationary unit is movable so that it can be repositioned to other environments or locations within the same environment; during monitoring the stationary unit may remain at the fixed location.

"Wearable Monitoring Unit" as used herein means a type of mobile monitoring unit that is affixed to or affixable to a wearer's body or clothing. In certain embodiments, it is affixable within the breathing zone of the wearer, which may be defined as a hemisphere that extends in front of the wearer's face and that has a radius of approximately 15 to 30 centimeters (or approximately 6 to 11 inches) measured from the midpoint of a line joining the wearer's ears, which is around the wearer's nose and mouth. In certain embodiments, the wearable unit is relatively small, e.g., no dimension is greater than about 2 inches (5 cm) or about 3 inches (8 cm).

Introduction

In many industries and certain environments (e.g., cities and areas were people work and reside), individuals such as workers may be exposed to harmful conditions, such as aerosols, gases, volatile organic compounds (VOCs), temperature, humidity, and noise. In some industries, governmental or other regulations set limits of acceptable levels and exposures to such conditions and it is therefore desirable to detect and monitor these potentially hazardous conditions. These regulations may also require that some environmental conditions be periodically or consistently monitored in order to detect the presence of harmful conditions and to determine that conditions have exceeded a particular threshold. In some instances, an industrial hygienist or other person may perform testing or sampling in order to monitor and determine such conditions which may be input to one or more industrial hygiene reports.

However, many traditional techniques and monitors for detecting and monitoring environmental conditions have serious drawbacks. For instance, many monitors do not provide real-time monitoring, but instead collect data at one location which is later analyzed at another location, such as a laboratory. For instance, the industrial hygienist may take samples of a particular industrial location, like a construction site, and then send those samples to a laboratory for processing and analysis. Additionally, some traditional monitors and techniques are not performed within the appropriate locations. For instance, the most accurate airborne exposures are performed within a person's breathing zone (the hemisphere that extends in front of a person's face and that has a radius of approximately 15 to 30 centimeters (or approximately 6 to 12 inches) measured from the midpoint of a line joining the that person's ears, which is around the person's nose and mouth), but many monitors and techniques do not take measurements from within this area. Furthermore, traditional monitors and techniques have limited sensing and output capabilities. Some conventional monitors and techniques may be limited in the size and type of particles detected, and may only output raw, sensed data and not data relating to exposure levels, or time weighted averages of exposures.

Example Systems

Disclosed herein are systems and techniques for monitoring environmental conditions. FIG. 1 depicts a first example system 100 for monitoring environmental conditions. System 100 includes a first monitoring unit 102, a remote computing unit 104 (e.g., a cloud computing unit), and a communications link 106 between the first monitoring unit 102 and the remote computing unit 104. The first monitoring unit 102 may be a mobile, stationary, or wearable monitoring unit. The first monitoring unit 102 may include one or more sensors, such as an air quality sensor 108, a temperature sensor 110, a pressure sensor 112, a relative humidity sensor 114, an accelerometer 116, a gyroscope 118, and a microphone 120. In some embodiments, the first monitoring unit 102 may also include a camera and/or other sensors, such as an air sampler and gas sensors, which are discussed in more detail below. The first monitoring unit 102 also includes a processor 122 with a first communications unit 124, and includes a memory 126 and a power management unit 128 which may include a battery, and a power interface, such as a USB interface. The remote computing unit 104 may have one or more processors 130, one or more memories 132 that stores instructions, and a second communications unit 134. In certain embodiments, a cloud or other remote computing infrastructure may be substituted by a local or quasi-local computing infrastructure such as an edge network or a local mesh network.

The first monitoring unit 102 may be considered a local component while the cloud processor may be considered a remote component. "Local" in the context of this application means an area or environment that is being monitored or controlled. For example, the first monitoring unit 102 is typically deployed locally in the environment to be monitored, such as a factory or refinery. "Remote" in the context of this application means in a location outside of the monitored environment, such as a different room, building, city, or country. In some embodiments, computationally intensive processing may be conducted remotely, e.g., not on the local first monitoring unit 102 but instead on remote computing resource 104, such as a cloud computing resource. Doing the computationally intensive processing on the remote computing unit 104 may provide advantages in certain contexts. For example, it may preserve battery life of batteries in the first monitoring unit 102, allow for a relatively simple processor 122 or other computational resources on the first monitoring unit 102, decrease processing time, and/or allow for the use of other data or information that is stored within the remote computing unit 104. In certain embodiments, the processing and/or storage requirements for environmental monitoring are shared between local monitoring unit 102 and remote computing unit 104.

Various criteria and/or heuristics may be employed to divide computation between the local and remote resources. For example, the division can be tuned to balance power consumption (given the size of the device) versus data communication bandwidth. For example computations pertaining to the inversion of particle size data from the sensor response maybe processed locally while corrections to this data may be done remotely using cloud and/or edge resources. Similarly, for an activity detection algorithm, the high resolution data maybe processed locally and some aggregated data transmitted to the cloud or other remote location to determine activity. For noise monitoring, noise waveforms captured locally may be processed locally and only aggregated noise exposure (dbA) values transmitted to the cloud or other remote location. Activation of alarms maybe triggered by local computation that compares locally generated measurements against thresholds that have previously been set remotely or fed into the device. If the device is disconnected, the device may still perform all the local notification functions, as needed.

The communication between local devices and remote units may be two-way. For instance, data generated by the sensors 108-120 (e.g., air quality data, temperature data, motion data, etc.) may be stored in the memory 126 on the first monitoring unit 102 and/or may be transmitted to the remote computing resource 104 as indicated by two-way arrow 106. Additionally, other sensor and first monitoring unit data and information may be transmitted to the remote computing unit 104, including sensor health, sensor operating parameters (e.g., measurement periods, sampling rates, power of a laser in the air quality sensor 108, etc.), battery parameters/health, position data and software version. The remote computing unit 104 may also transmit data and instructions to the first monitoring unit 102, such as sensor software or firmware updates, changes to sensor operating parameters, and alarms, for instance. The two-way arrows on the first monitoring unit 102 further illustrate the two-way data transmission between components of the first monitoring unit 102.

Various communication protocols and mechanisms for delivering information between the local monitoring units, e.g., between wearable and stationary monitoring units, and/or between the local monitoring units and remote units, e.g., the remote computing unit 104, may be used. In some instances short-range wireless communications may be used between a local monitoring unit and a local network unit such as a WiFi modem or other transceiver which may include, WiFi (802.11b/g/n 2.4 GHz), LiFi, Bluetooth (e.g., Bluetooth low energy, enhanced data rate), and nearfield communications. In some instances, the local network unit may use a wireless or wired link to the internet. In some examples, communication between the local monitoring units and between the cloud computing unit and the local monitoring units may use low power, long range wireless IoT communication protocols such as LoRaWAN LPWAN (narrowband IoT (NB-IoT)), and Cat M1 (LTE Cat M1). Additionally, communication between the local monitoring units and between the cloud computing unit and the local monitoring units may use conventional cellular communications protocols such as 3G, 4G, and 5G. Similarly, the system may have hardware and/or software supporting global positioning satellite ("GPS") or other location determining protocol (e.g., by WiFi or any other signal triangulation determined from access points).

For instance, the first communications unit 124 on the first monitoring unit 102 may have cellular communications hardware for receiving and transmitting data over a cellular protocol. The first communications unit 124 may also have a GPS antenna that can establish a connection with multiple GPS satellites. Using data from communications with such satellites, the first communications unit 124 can determine the location of the first monitoring unit 102. The term "GPS" herein may mean the broader concept of a location system employing one or more satellites that transmit ephemeris (e.g., a table or data file that gives the calculated positions of a satellite at regular intervals throughout a period) and/or position fixing data to a GPS receiver or antenna on a device. The location of the monitoring unit may be calculated from the position fixing data on the unit itself—first communications unit 124 in this case. Multiple satellites may be used in the system with each one communicating ephemeris data and/or position fixing data. The same satellite may communicate both ephemeris data and position fixing data, or ephemeris data and position fixing data may be communicated through separate satellites. The satellites may be satellites in a GPS system, or it may be satellites in another satellite system such as the Russian Global Navigation Satellite System, the European Union Compass system, the Indian Regional Navigational Satellite System, or the Chinese Compass navigation system.

Some GPS systems use a very slow data transfer speed of 50 bits per second, which means that a GPS receiver, in some cases, has to be on for as long as 12 minutes before a GPS positional fix may be obtained. Once a positional fix is obtained, subsequent positional fixes may take much less time to obtain (assuming that the subsequent positional fix occurs within a sufficiently close interval), but this initial lock-on period requires that the GPS receiver be powered for the entire initial lock-on, which can be taxing on devices with small battery capacities.

As stated above, the remote computing unit 104 may have one or more processors 130, one or more memories 132 that stores instructions, and a second communications unit 134 that are all communicatively connected, e.g., wirelessly or hard-wired, to each other. In some instances, one or more servers may include the one or more processors 130, the one or more memories 132, and the second communications unit 134. Therefore, the term "server" is not limited to a single hardware device, but rather include any hardware and software configured to provide the described functionality. The second communications unit 134 may use any of the communications protocols described above for transmitting and receiving data from the local monitoring devices and any other device.

The one or more memories 132 may be any combination of one or more memory devices, short term, and/or long term memory. Aspects of the disclosure described below may be implemented by various types of hardware, software, firmware, etc. For example, some features of the disclosure may be implemented, at least in part, by non-transitory, machine-readable media that include program instructions, state information, etc., for performing various operations described herein. Examples of program instructions include both machine code, such as produced by a compiler, and files containing higher-level code that may be executed by the computer using an interpreter. Examples of non-transitory, machine-readable media include, but are not limited to, magnetic media such as hard disks with rotating media, floppy disks, and magnetic tape; optical media such as CD-ROM disks, digital versatile disk (DVD); magneto-optical media; semiconductor memory such as flash memory devices, nanosystems (including molecular memory ICs), or any type of media or device suitable for storing instructions and/or data. Hardware elements configured to store and perform program instructions may be read-only memory devices ("ROM") and/or random access memory ("RAM"). Similarly, any of these types of memory may be provided locally, such as on local unit 102.

Additionally, a computer program product implementation includes a machine-readable storage medium (media) having instructions stored thereon/in which can be used to program a computer to perform any of the processes of the implementations described herein. Computer code for operating and configuring the remote computing unit 104 to communicate with local monitoring units and/or to process data as described herein may be stored on any of the types of physical memory described above. Additionally, the entire program code, or portions thereof, may be transmitted and downloaded from a software source over a transmission medium, e.g., over the Internet, or from another server, or transmitted over any other conventional network connection (e.g., extranet, VPN, LAN, etc.) using any communication medium and protocols (e.g., TCP/IP, HTTP, HTTPS, Ethernet, etc.). It will also be appreciated that computer code for implementing implementations can be implemented in any programming language that can be executed on a client system and/or server or server system such as, for example, C, C++, HTML, any other markup language, Java™, JavaScript®, ActiveX®, any other scripting language, such as VBScript, and many other programming languages as are well known may be used. (Javan™ is a trademark of Sun Microsystems®, Inc.).

The one or more memories 132 of the remote computing unit 104 may include one or more databases for storing data. The databases can be implemented as single databases, a distributed database, a collection of distributed databases, a database with redundant online or offline backups or other redundancies, etc., and might include a distributed database or storage network and associated processing intelligence. In some embodiments, the cloud computing unit 104 may be able to access the databases of a data provider that provides or allows access to data collected or stored by that data provider, such as weather data from weather.com©.

In certain embodiments, the remote computing unit 104 may be configured with a high level of security. For instance, the United States Federal Risk Authorization Management Program (FedRAMP) may provide a standardized approach to assessment, authorization, security, and continuous monitoring for cloud products and services. This may include the National Institute of Standards and Technology (NIST) SP 800-53 security controls. The remote computing unit 104 may utilize processes and procedures that are FedRAMP compliant. In some embodiments, other protocols may be used for storage, security, and/or validation, including data stored across multiple computers or servers that are linked in a peer-to-peer network, such as blockchain or IOTA.

Figure 2:
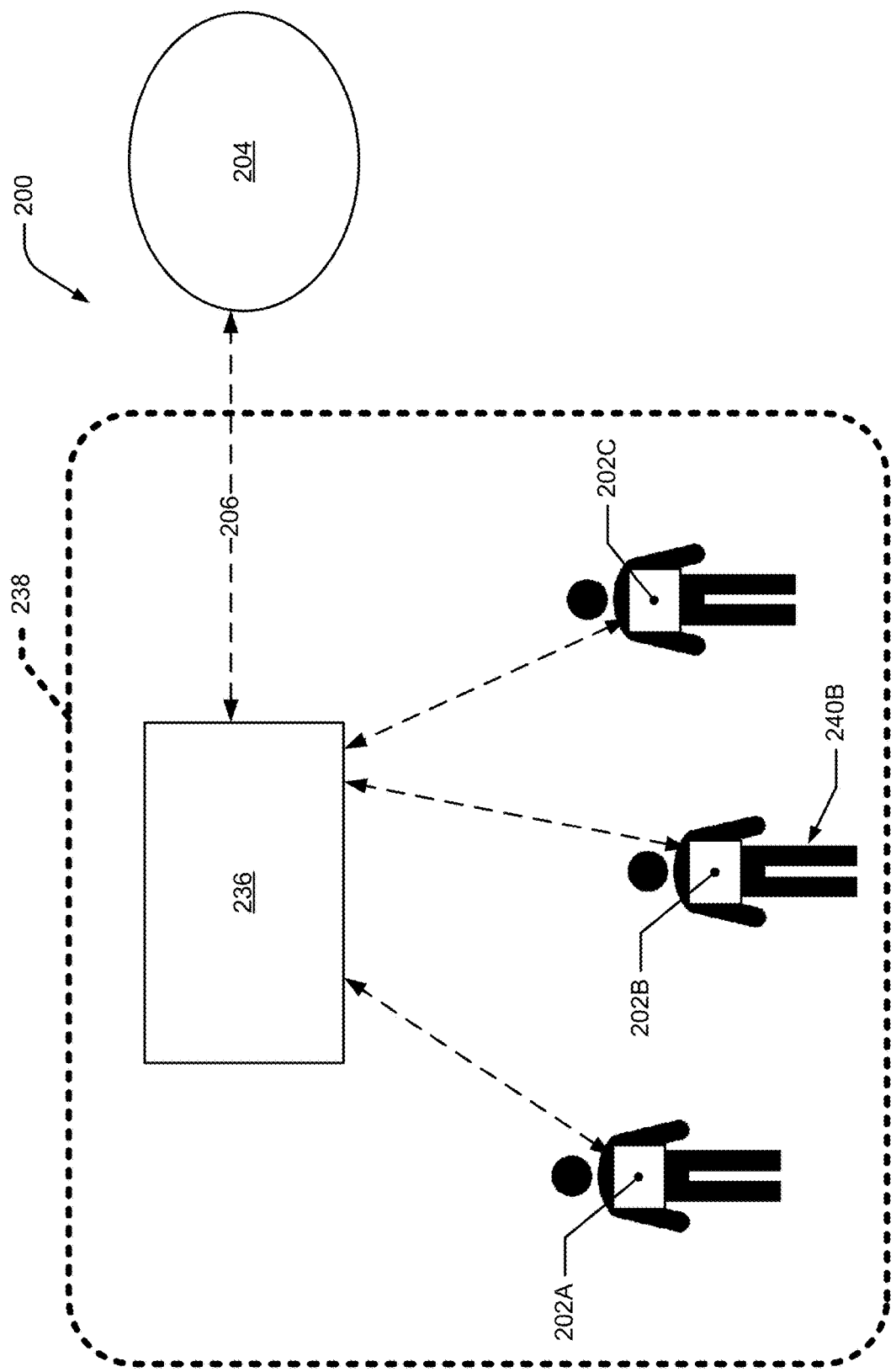
FIG. 2 depicts a second example system for monitoring environmental conditions.

Multiple local monitoring units may be interconnected in various ways. For example, one or more local mobile monitoring units may be directly communicatively connected with a local stationary unit that is directly communicatively connected with a remote computing unit. FIG. 2 depicts a second example system for monitoring environmental conditions. As can be seen, the second example system 200 includes three local mobile monitoring units 202A, 202B, and 202C, a stationary unit 236, and remote computing unit 204. The environment that is to be monitored is represented by the bold dotted line 238; in some embodiments, the area within this environment 238 may be considered the local area. Each mobile monitoring unit 202A-202C may be configured like mobile monitoring unit 102 such that they each include one or more sensors that generate data regarding measured and detected conditions, for example air quality, temperature, humidity, and pressure. Each mobile monitoring unit 202A-202C is also mobile and at least two are wearable by individuals, one of which is labeled 240B, in that person's breathing zone. Data may be transmitted between each mobile monitoring unit 202A, 202B, and 202C, and the stationary unit 236 as indicated by the dashed double-sided arrows.

The stationary unit 236 is positioned within the environment 238 in a fixed location relative to mobile monitoring units 202A-202C. The stationary unit also includes a communications unit (not depicted) such as those described above that enable it to transmit and receive data with each mobile monitoring units 202A-202C, and to transmit and receive data to and from the cloud computing unit 204 as indicated by double sided arrow 206. In some instances, the stationary unit 236 may be hard-wired to power and communications interfaces(s), such as DSL, Ethernet, and fiber-optic. The stationary unit 236 may therefore serve, in some embodiments, as a communications hub which presents multiple advantages. For example, depending on the configuration of the mobile monitoring units and the environment, the mobile units may not be able to connect directly with the cloud computing unit. For instance, the local monitoring mobile units may not have the communications protocol necessary to communicate directly over the Internet to the cloud computing unit (e.g., they may only have local WiFi communications protocol). In some instances, even if the mobile monitoring units do have the ability to communicate over the Internet (e.g., by having cellular capability), the mobile monitoring units may not have adequate reception to reach the Internet or other network. In such instances, it may be desirable to have a local stationary unit that has a wired or more powerful wireless connection that can communicate directly over the Internet or other network to the remote computing unit.

In some implementations, the stationary unit 236 may be a monitoring unit like monitoring unit 102 described above such that it contains one or more sensors to measure a condition in the environment 238. In some other embodiments, the stationary unit 236 may be placed outside the environment 238 that is to be monitored, unlike depicted in FIG. 2.

Figure 3:
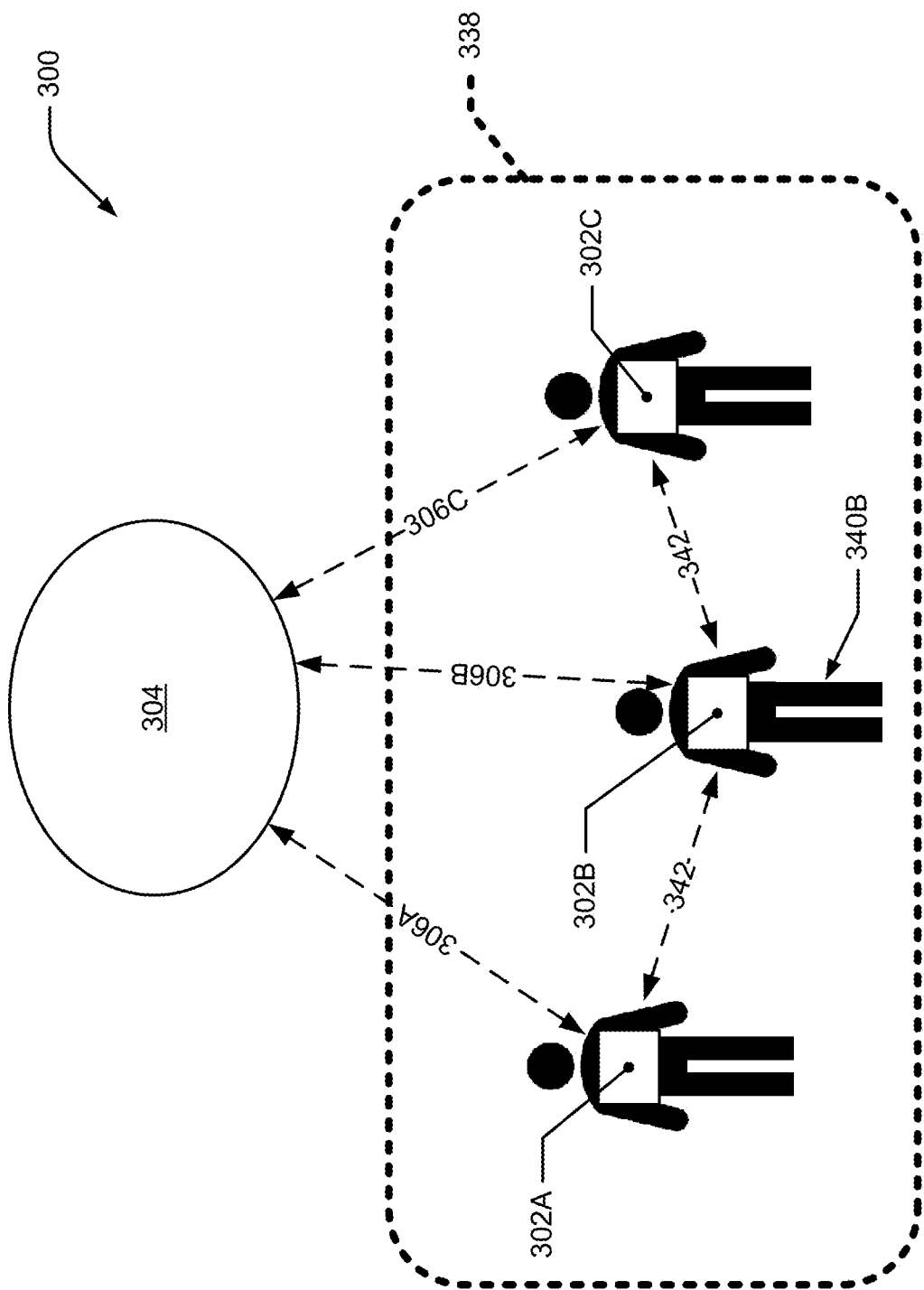
FIG. 3 depicts a third example system for monitoring environmental conditions.

In another network example, one or more local mobile monitoring units may be directly communicatively connected with the cloud computing unit as seen in FIG. 3 which depicts a third example system for monitoring environmental conditions. The third example system 300 includes three local mobile monitoring units 302A, 302B, and 302C and remote computing unit 304. The environment that is to be monitored is represented by the dotted line 338 in which the local mobile monitoring units 302A, 302B, and 302C are positioned. As with example system 200, each mobile monitoring unit 302A-302C may be configured like mobile monitoring unit 102 and each is mobile and at least two are wearable by individuals, one of which is labeled 3406, in that person's breathing zone. Similar to FIG. 1, data may be wirelessly transmitted directly between each mobile monitoring unit 302A, 302B, and 302C, and the cloud computing unit 304 as indicated by the dashed double-sided arrows labeled 306A-306C, respectively. This wireless communication includes any of the examples described above.

In some embodiments, as further depicted in FIG. 3, the mobile monitoring units 302A-302C may be wirelessly connected to each other, as indicated by double sided arrows 342. This enables data to be transmitted and received between each of the mobile monitoring units 302A-302C. This wireless communication protocols may again include any of the examples described above. In certain embodiments, three or more of the mobile monitoring units collectively communicate to form a dynamic network such as a mesh network.

Monitoring Units

Figure 4:
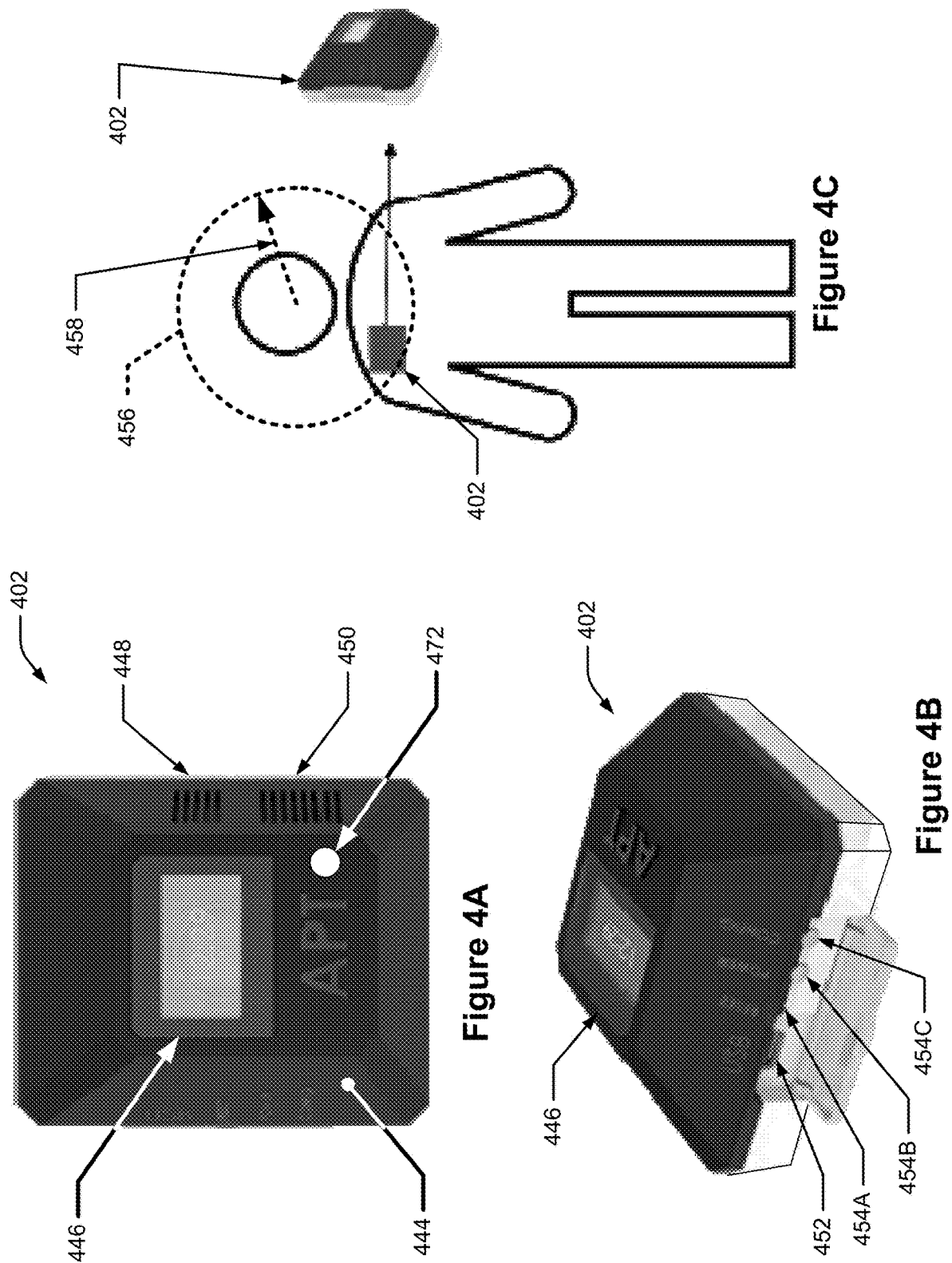
FIGS. 4A and 4B depict plan and off-angle views of an example mobile monitoring unit.
FIG. 4C depicts the example mobile monitoring unit positioned within a wearer's breathing zone.

Additional details of the monitoring units will now be presented. Each monitoring unit, such as the first monitoring unit 102 of FIG. 1, may include a case that encompasses the components of the monitoring unit. FIGS. 4A and 4B depict plan and off-angle views of an example mobile monitoring unit. In FIG. 4A, the mobile monitoring unit 402 includes a case 444 that encompasses the unit's internal components, such as those described herein, a display for a user interface such as a graphical user interface (GUI) 446, an inlet 448, and an outlet 450. In FIG. 4B, the mobile monitoring unit 402 also includes a power interface 452, such as a USB interface, where a power cord may be connected to the mobile monitoring unit 402 to charge its battery, as well as inputs 454A, 454B, and 454C, that may be buttons and that provide, when actuated, an input to a component of the mobile monitoring unit 402 such as the processor 422 or a sensor. For example, input 454A may be a reset button that causes the mobile monitoring unit 402 to restart, input 454B may be a power button that causes the mobile monitoring unit 402 to turn on and off, and input 454B may be a configuration button that causes the mobile monitoring unit 402 to be programmed or configured. In some embodiments, the power interface 452 may also be a port configured to transfer data, which includes a cable port, such as the USB port. In some instances, the power interface 452 may be configured to charge wirelessly or charge through a docking station.

The case 444 may have various shapes, such as generally rectangular as depicted in FIG. 4A, as well as circular, oval, or any other shape. The size of the case 444, and thus the size of the mobile monitoring unit 402, may be less than three inches in each measurement dimension, and less than two inches in some embodiments. The size may also be small enough to fit into the palm of a user's hand. In some instances, the dimensions may be 3.0 in ×2.75 in ×1.25 in (L×W×H).

The case 444 may also include attachment features that enable the mobile monitoring unit 402 to be worn by and affixed to a user. These features may include a clip, clamp, chain, band, lanyard, wristband, buckle, slots to receive a strap, straps, ties, and the like. As stated above, these features enable the mobile monitoring unit 402 to be worn in the wearer's breathing zone. FIG. 4C depicts the example mobile monitoring unit 402 positioned within a wearer's breathing zone 456 which, as stated above, may be considered a hemisphere that extends in front of the wearer's face and that has a radius 458 of approximately 15 to 30 centimeters (or approximately 6 to 11 inches) measured from the midpoint of a line joining the wearer's ears, which is around the wearer's nose and mouth. In certain embodiments, the wearable unit is relatively small, e.g., no dimension is greater than about 2 inches (5 cm) or about 3 inches (8 cm).

As stated above, the monitoring unit 102 includes one or more sensors configured to detect, determine, and monitor one or more environmental conditions. To enable at least some of this detection, the inlet 448 and the outlet 450 of the case 444 allow air, pressure, liquid, and other environmental elements to reach the one or more sensors. One of the environmental conditions detected by the monitoring unit 102 is particles in the air. The air quality sensor of the monitoring unit 102 (and the mobile monitoring unit 402) is configured to detect and measure various parameters of particles in the air surrounding the monitoring unit 102. The air quality sensor 108 may be a counter sensor that has a laser which emits a beam through which particles pass and that measures and counts the beam pulses to determine particle counts and sizes.

Figure 5:
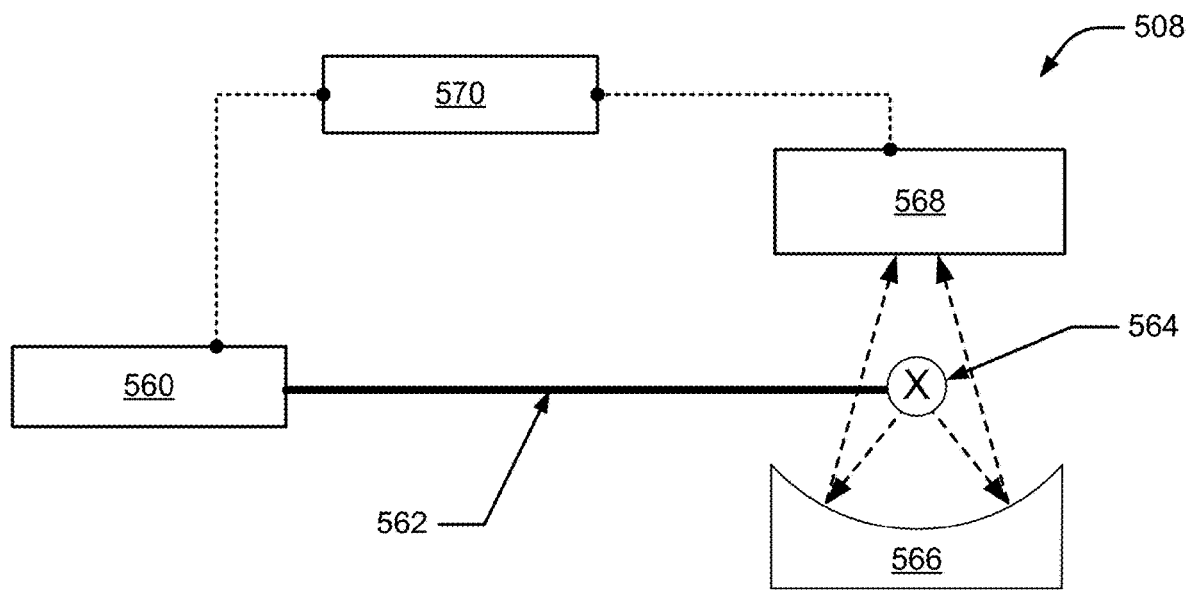
FIG. 5 depicts a schematic of an example air quality sensor.

FIG. 5 presents a schematic of an example optical air quality sensor. This sensor 508 may be used as air quality sensor 108 of FIG. 1, which may be included on the mobile monitoring unit 402. Here, the air quality sensor 508 includes a light source 560 such as a laser that emits a light beam 562 and is configured to allow particles (a single particle 564 is illustrated) to pass through the beam 562. Sensor 508 optionally includes a mirror 566 and a detector 568. The laser may be a diode laser source. In some embodiments, the air quality sensor 508 has a fan or pump to push or pull air into the air quality sensor 508, through the inlet 448, which, in some embodiments, directs particles to pass through the laser beam 562. In FIG. 5, the particles are shown travelling through the air quality sensor 508 in a direction perpendicular to the beam 562 and to the plane of the page, as indicated by the "X" in the particle 564. As the particle 564 passes through the beam 562, the particle 564 interacts with the beam 562 to cause light to scatter off the particle, onto the concave mirror 566, and into the detector 568 which is configured to detect and capture this optical signal as a measurable pulse.

The air quality sensor 508 generates signals responsive to the particles that pass through the beam 562. In some embodiments, the raw signals generated by the air quality sensor 508 include the number of pulses and the sizes of the pulses measured by the detector 568. The air quality sensor 508 may also include logic 570 (e.g., a processor and instructions) that is configured to interpret the measured pulses and generate additional data, such as particle count and particle size. For particle count, these measured pulses over a time period provide a frequency which may correlate to a particle count. Additionally, each pulse may correlate to a single particle and the total number of measured pulses can be correlated to the total number of particles that passed through the air quality sensor 508. Also, the measured pulse height may correlate with the particle size. In some implementations, the particle volume, and by implication the particle's mass, influences pulse height. The data generated about particle mass may not be the exact size, but rather may be categorized into one or more size "bins" which indicate that that mass of each particle falls within a specific size range. For example, the air quality sensor 508 may generate particle mass data for particle mass (PM) 0.3, PM0.5, PM1.0, PM2.5, PM4.0, PM5.0, and PM10. In some examples, the air quality sensor 508 may detect particles that fall under each size bin, e.g., particles less than PM0.3 or less than PM2.5, and not the particle masses within the size bin. This generated data may also include the particle count for each size bin.

In some embodiments, the operating parameters of the air quality sensor 508 may be changed, including the laser power and the pulse height threshold. These adjustments may result in different detected bin sizes and frequency period. For example, decreasing the power of the laser may decrease the detectable size bins or a calibration coefficient of the sensor. Further, changing the air flow to the sensor may change the accuracy and operating range of the device. In certain embodiments, an additional dynamic flow system is incorporated to provide real-time dilution to increase the maximum concentration detectable by the unit. So if concentration is too high, the dilution system may mix sample air with filtered air to reduce the concentration of particles that are then measured by the sensor. An appropriately configured processor may invert the concentration based on the dilution factor to the original undiluted concentration.

In certain embodiments, a monitoring unit includes one or more duplicate sensors for, e.g., calibrating and determining inaccuracies and drift of one of the sensors. In some cases, a duplicate sensor is provided on a fixed monitoring unit. A comparison of simultaneous measurements by two sensors may indicate whether one of the sensors (e.g., one on a wearable unit) has drifted or is inaccurate if these simultaneous measurements are different from each other by a particular threshold. Similarly, during calibration, if these simultaneous measurements are within the particular threshold, then they may be properly calibrated and accurate. For example, it has been discovered that during operation of the air quality sensor 508, particles can deposit on and around the detector 568, mirror 566, and other aspects of the air quality sensor 508 which can cause inaccuracies in the sensor's measurements. The longer the air quality sensor 508 operates, the more particles that deposit within the sensor. In some implementations, referring back to FIG. 1, the monitoring unit 102 may have two duplicate air quality sensors 108. The first of these air quality sensors may be used for regular and continuous monitoring while the second air quality sensor may only be used periodically to provide a simultaneous duplicate measurement that can be compared to the measurements of the first air quality sensor.

The instructions stored on the one or more memories 126, or in the remote computing unit 104, may cause the processor 122 to take simultaneous measurements from the two air quality sensors 108 for a particular time period and the measurements generated by these two sensors may be compared against each other to determine whether they differ more than a threshold which may indicate that the first sensor has become inaccurate or drifted. In some instances, the detected inaccuracy or drift of the first sensor may be used as a correction factor to adjust the measurements of the first sensor. For example, if it is determined that the first sensor is off by 5%, then a 5% correction factor can be applied to its subsequent measurements.

In addition to one or more air quality sensors, the first monitoring unit 102 may also include one or more non-particle sensors as stated above. This may include the temperature sensor 110 for determining a temperature around the unit and which may be a thermocouple, resistance temperature detector, negative temperature coefficient thermistor, for example; the pressure sensor 112 for determining the pressure around the unit and which may be a pressure transducer, a pressure transmitter, a pressure sender, a pressure indicator, a piezometer, and a manometer; and the relative humidity sensor 114 for determining the humidity around the unit and which may be capacitive, resistive, and thermally conductive sensor. As discussed in more detail below, the data from these sensors may be used to correct and adjust the data generated by other sensors. For example, the detected particle count may be affected by, or dependent upon, temperature, relative humidity, and pressure, and the instructions stored on the one or more memories 126, or in the cloud computing unit 104, may cause the processor 122 or the one or more processors 130 in the cloud computing unit 104 to adjust, based on one or more of the temperature, relative humidity, and pressure, the detected particle count to a determined particle count.

Other sensors of the monitoring unit, like discussed above, may include an accelerometer 116, such as a triaxial, a bulk micromachined capacitive, electromechanical, and the like; a gyroscope 118 such as a rate and rate-integrating; and a microphone 120 such as a dynamic, condenser, piezoelectric, carbon, and ribbon.

The instructions stored on the one or more memories 126, or in the remote computing unit 104, may cause the processor 122 to operate any one of the sensors on the first monitoring unit 102, to store the data generated by each of the sensors on the one or more memories 126 on the unit, and to transmit the data generated by each of the sensors to another unit, such as another mobile monitoring unit, the stationary unit, and the cloud computing unit 104. In some of the embodiments that include the display 446, the instructions may also cause at least some data generated by the sensors to be displayed on the display, such as particle count, temperature, and relative humidity, for example. Instructions stored in the cloud computing unit 104 may also cause the processor to change the operating parameters of any one of the sensors, such as the sample rate of the temperature sensor 110.

The display 446 may be configured to display information to a person, such as a wearer of a mobile monitoring unit. In some implementations, the display 446 may be a liquid crystal display (LCD) or a light emitting diode (LED) display (e.g., an OLED display); the display 446 may also be black and white, or color. In some embodiments, displays may show sensor reading values (e.g. PM concentration), risk factors, temperature/humidity data, visual indicators of risk (e.g. red for dangerous levels of high concentration, green for safe levels), and real time TWA analysis.

In some embodiments, the first monitoring unit 102 may also include a camera that may face out from case of the monitoring unit for capturing imaging data such as photographs, video, or both. Referring back to FIG. 4, the monitoring unit 402 includes a camera 472 that faces out from the case 444; FIG. 1 also includes the camera 172. In certain embodiments, a camera may have a rotatable angle of view; for example, a camera may be mounted on a hinged or similar part. Like the sensors, the camera 172 is communicatively connected to the processor 122. Some example cameras include omnivision image sensors with appropriate lenses, such as wide angle lens, which may be used to image a large area. The instructions stored on the one or more memories 126, or in the remote computing unit 104, may cause the processor 122 to operate the camera 172 to record video and/or photographs, store them on the one or more memory 126, and to transmit the video and/or photographs to the remote computing unit 104. Instructions stored in the cloud computing unit 104 may also cause the processor to change the operating parameters of the camera 172, such as its operating mode to capture video or photographs, as well as the rate at which videos and photographs are taken, such as photographs every 10 seconds, every 30 seconds, and video at different framerates, such as 24 frames per second (fps), 30 fps, 60 fps, 120 fps, 240 fps, and 300 fps.

In some implementations, a camera's operation is tied to local sensor outputs. In certain embodiments, the camera only record images when the sensor parameters, as interpreted by camera control logic, trigger the camera to record. On application of a camera is to diagnose an issue or condition that may have caused a detected increase in particulate matter or noise. The camera control logic may control camera operation in a way that gathers only relevant images/videos (e.g., when sensor readings indicate a need for additional information about the local environment or the activities currently being conducted).

As noted above, the first monitoring unit 102, including the communications unit 124, may have a positioning sensor, such as a GPS antenna that may determine the position of the first monitoring unit 102. This GPS antenna may be integrated with a processing chip that includes the processor 122 and the memory 126.

In some embodiments, the first monitoring unit 102 may include a notification mechanism that is configured to present to a person with a notification, such as an alarm or alert. For stationary monitoring units, this may include presenting persons within a particular spatial proximity from the stationary monitoring unit with the notification; for mobile monitoring units such as wearable monitoring units, this may include presenting the wearer of the monitoring unit with the notification.

The "notification" may be one or more of an alarm, alert, message, an auditory output, an electronic communication, an electromagnetic communication, a visual output, and a tactile output. Notifications may be provided through a variety of media, and may, in some cases, require further action by an intermediate device before being perceptible by the person. For example, the monitoring unit may have a notification mechanism that includes a display or lights that are configured to display graphics or light up in order to catch the attention of a person (the notification, in this case, may refer to a signal that is sent to the lights or display that cause these components to light up or display graphics to a person; it may also refer to the light or graphics that is emitted or displayed by components receiving the signal in response to the signal). In FIG. 1, the notification mechanism 174 is represented by circle 174. In some examples, the monitoring unit may have a notification mechanism that includes a speaker or other device capable of generating auditory output that may be used to provide the notification (the notification in this case may be a signal that is sent to a speaker or other audio device; it may also refer to the actual audio output that is generated by the audio device in response to the signal).

In some other or additional examples, the notification mechanism may include a wireless interface and the notification may take the form of an electronic or electromagnetic communication, e.g., a wireless signal, that is sent to another device, e.g., a monitoring unit or a smartphone, associated with the person (the notification in this case may be an electromagnetic signal; it may also refer to any audio, visual, tactile, or other output generated by the receiving device in response to receipt of the signal). In such scenarios, the notification may still be generated or initiated by the notification mechanism even if the intended recipient device of the communication fails to be activated or otherwise fails to convey the notification to the person. The notification mechanism may be configured to generate and/or provide one or more notifications to the user, and may include one or more components that may be used to generate audio, visual, tactile, electromagnetic, or other types of notifications.

As stated above, the power management unit 128 seen in FIG. 1 may include a battery. In some implementations, the battery may be rechargeable, such as a lithium-ion, nickel cadmium, or nickel metal hydride for instance. The battery is configured to provide a reasonable discharge time under normal operation, such as about 4 hours, 8 hours, 10 hours, and 12 hours. The battery may also be configured to provide information regarding the state of the charge (SOC) and state of health (SOH) of the battery. This information may include charge acceptance, internal resistance, voltage, and self-discharge. The battery of the power management unit 128 is used to power any feature of the monitoring unit 102, such as the processor 122, the notification mechanism 174, the communications unit 124, and any one of the sensors. In some embodiments, one or more of the sensors on the monitoring unit 102 may be "active" such that it requires an external source of power to operate. The air quality sensor 108 described above, including sensor 508 in FIG. 5, may be an active sensor because it may use a pump or fan to push or pull air into and through a chamber of the sensor. One or more of the sensors on the monitoring unit 102 may be passive in that it detects and responds to an input from the physical environment, such as detecting vibrations, light, heat, and radiation, for instance. For example, the temperature sensor 110, the pressure sensor 112, and the relative humidity sensor 114 may be passive sensors.

In some embodiments, the monitoring unit 102 may include a filter sample cartridge and pump, represented as item 176 in FIG. 1. The pump is configured to push or pull air into the filter sample cartridge which collects the particulates and elements in the air. The filter sample may be removed from the monitoring unit 102 and analyzed offline, such as in a laboratory or remote location. The analysis results may be entered as data into the cloud computing unit 104 or to the monitoring device 102 and used to calibrate, adjust, and correlate data generated by the monitoring unit. For example, the air quality sensor 108 and the filter sample cartridge and pump may be simultaneously operated, and the particle count and size data detected and generated by air quality sensor 108 can be compared to the size, particle count, and other particle information measured by and determined from filter sample cartridge results. This correlation may be used in subsequent monitoring when a monitoring unit is working in the same environment. For instance, the correlation may indicate that the particle count data generated by the air quality sensor 108 is offset from the actual particle count of the air by a first correction factor and this first correction factor can be applied to future data generated by the air quality sensor 108 so that the detected results align with the results measured by filter sample cartridge. In another instance, filter sample results may indicate the type or types of particles that were detected, such as silica or lead, and these known particles can be correlated with the detected particles and other data generated by the monitoring unit.

The operation of the filter sample cartridge and pump, such as the flow rates and operation times, may vary and may be configured to provide comparative sensor data. For example, the filter sample cartridge and pump may be caused to operate, by the processor executing instructions in the memory or the cloud computing unit, and collect air samples while the air quality sensor 108 is also operating. In some embodiments, the filter sample cartridge and pump are integrated into a mobile monitoring unit and a stationary monitoring unit. In some other embodiments, the filter sample cartridge and pump may be separate from any monitoring unit, but may be positioned in close proximity to the monitoring unit in order to sample air and provide correlation data like described above.

Figure 6:
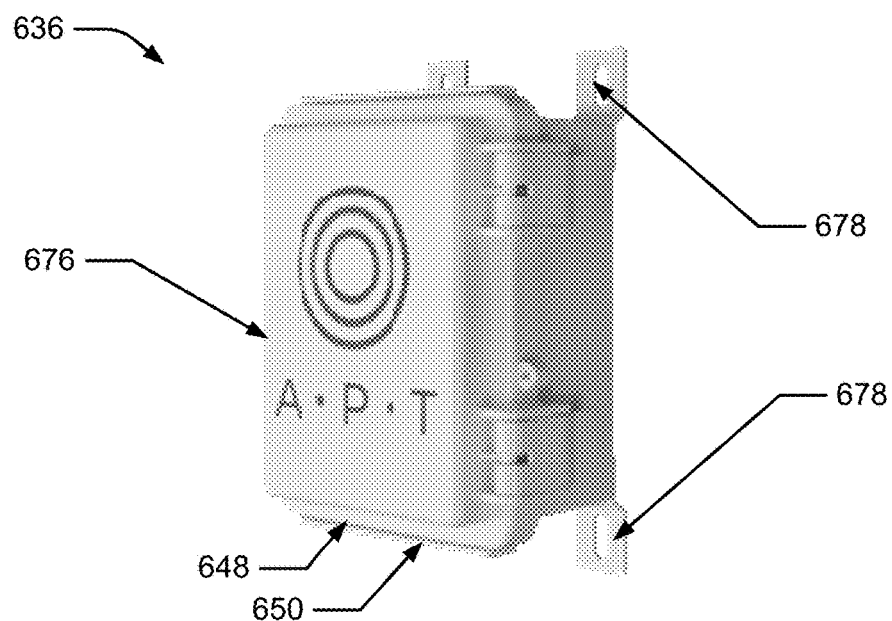
FIG. 6 depicts an example stationary monitoring unit.

As mentioned above, some monitoring units may be considered stationary monitoring units that are non-wearable and fixed in a position. FIG. 6 depicts an example stationary monitoring unit 636 which may be like stationary monitoring unit 236 described above. In some embodiments, the stationary monitoring unit 636 may have the same features as the monitoring unit 102 of FIG. 1, such as the air quality sensor 108, the temperature sensor 110, the pressure sensor 112, and the relative humidity sensor 114, and the communications unit 124 and the power management unit 128. However, the communications unit 124 of the stationary unit 636 may be different than that of the mobile monitoring unit, such as having hard-wired communications interfaces, e.g., for DSL, Ethernet, and fiber-optic connections; it may also have more powerful wireless antennas than a mobile monitoring unit. The power management unit 128 may also be configured to receive hard-wired power, such as from a wall outlet or building electricity, which may be 110 volts or 220 volts, and may be 15 amp and 20 amp circuits.

Some stationary units may also have a different case than mobile monitoring units. As seen in FIG. 6, stationary monitoring unit 636 includes a hinged lid 676 and mounting features 678 for securing the stationary monitoring unit 636 to a fixed location, such as a wall or post. The hinged lid 676 allows for direct access to the unit's components, such as its buttons and the power management unit (which may be a battery or hard-wiring), as well as offering the weather protection for the unit. In some instances, the stationary monitoring unit 636 has an inlet 648 and an outlet 650, like described above, in order to allow the unit's sensors to detect environmental conditions. For additional weather protection, the inlet 648 and outlet 650 may be positioned on the bottom of the unit.

Example Data Analysis Techniques

The monitoring systems and apparatuses described herein may use various data analysis techniques, which may be implemented as executable processes or algorithms, to measure and/or determine desired metrics. These metrics may provide raw data, signals, or other information. Examples or measured metrics include particle count, particle size, particle mass, temperature, relative humidity, and pressure, for instance. The determined metrics may be calculated values that include, for example, the types of materials detected (e.g., silica, lead) and metrics that have been adjusted or corrected to account for other variables (e.g., a particle count adjusted to account for the pressure and humidity).

Various computational techniques described herein may use multiple inputs. As mentioned herein, some of these inputs include the raw sensor data generated by the one or more sensors of a monitoring unit. This data can include, for example, a particle count over a time period and particle size (e.g., particle masses within bin sizes PM0.3, PM0.5, PM PM1.0, PM2.5, PM4.0, PM5.0, and PM10), temperature, humidity, pressure, acoustic signals (e.g., generated by a microphone), inertial signals (e.g., generated by a gyroscope or accelerometer), position data (e.g., GPS position data), and camera or video data. In some instances, this data may be raw or converted data. For example, as described above, the air quality sensor 108 may generate a pulse frequency which can be converted to a particle count over time, and may generate a pulse height which can be converted to particle mass size.

In addition to the data sensed by a monitoring unit, the techniques may also use data that was not sensed by the monitoring unit. This can include publicly available data which may be weather feeds and air quality indices, as well as particle compositional information from one or more material safety data sheets (MSDS). MSDSes may include information as to which hazardous materials, and at what percentages, are included in various materials; MSDSes may also indicate the acceptable OSHA exposure levels for the hazardous materials. For example, a MSDS for concrete may indicate that it includes 0-90% silica (by weight) and 15-25% calcium hydroxide (by weight), and may list the OSHA permissible exposure limit (PEL) based on a time-weighted average (discussed below). All of this data may be stored within a memory or database of the remote computing unit 104, or may be accessible by the one or more processors of the remote computing unit 104 such that it can be used by the one or more processors of the remote computing unit 104.

Similarly, computational techniques may use historical data from the same or other monitoring units. For instance, the data generated by one monitoring unit may be transmitted to and stored within the cloud computing unit 104 which can later be used by the cloud computing unit 104 for determinations related to that same monitoring unit. In some other instances, the data generated by one monitoring unit may be transmitted to and stored within the cloud computing unit 104 which can later be used by the cloud computing unit 104 for determinations related to other monitoring units. For example, one monitoring unit may have generated data at a specific location at one time and at a later time, this data may be used for another monitoring unit at that same specific location. Additionally, the data generated by one monitoring unit may be transmitted to other monitoring units that are currently with the same environment, like described above and depicted in FIG. 3.

In some implementations, one or more inputs include data and/or signals captured using sensors and/or an application on a user's phone, mobile device, and wearable electronic device, which may include using that device's sensor data, e.g., accelerometer, gyroscopic, and acoustic data, combined with separate monitoring unit (mobile or stationary) readings. In some instances, the techniques may run on the cloud with data aggregated from the phone and the monitoring unit.

In some embodiments, inputs to computational techniques may include data related to an activity or task being performed near a monitoring unit. For example, one or more of the sensors on the monitoring device may generate data that is related to or indicative of a particular activity or task. This may include the gyroscope, accelerometer, and/or microphone generated motion data and signals that can be associated with various activities or tasks, such as jackhammering, an explosion, and a gas release. In some instances, the data may indicate that a wearer of a mobile monitoring unit is performing the task or activity. For example, the gyroscope, accelerometer, and/or microphone may indicate that the wearer is jackhammering. In a similar example, the microphone of one mobile monitoring unit may indicate that the wearer is near, but not performing, the task, like jackhammering. Data from a microphone may further be indicative of particle sources from nearby operating machinery based on characteristic noise signatures of different equipment and machinery.

The techniques described herein may also, in some embodiments, use sensor parameters as inputs. This may include sensor health, battery parameters/health, current software version, and operating parameters, e.g., measurement periods, sample rate, and power of the laser for the air quality sensor 508.

The apparatuses and techniques of the present disclosure may provide any of various outputs. The content and form of an output variations may depend on the mechanism of presentation, such as via a dashboard, display, GUI, notifications of a notification mechanism, messages sent to user devices (e.g., text messages, email messages, phone calls to a user's phone), and instructions to a facility where the monitoring unit resides (e.g., shut down a machine that might be contributing to a dangerous condition, activate a system such as a ventilation system that can mitigate a dangerous condition, provide announcement to all personnel, etc.). Unless specified, the outputs described herein may be presented in any of these means.

In some embodiments, data characterizing particles may be an output of the apparatuses and techniques. This can include total particle counts, the time period of the total particle counts, particle concentration binned by size, particle mass per bin size, particle refractive index, particle fractal dimensions, chemical composition, particle volume, particle surface area, particle size distribution, particle mass within a known cutoff curve (e.g., PM 2.5, PM 4.0). Additional data from any of the sensors on the monitoring unit may be output, such as non-particle environmental information including temperature, humidity, pressure, gas composition, auditory signals (e.g., decibels). Output data may also include motion data, location data (e.g., GPS coordinates), communications information (e.g., signal strength to a communications node, like a cell tower, WiFi hub, or GPS satellites), battery data (e.g., charge level, lower battery, undergoing charging), and sensor data (e.g., whether a sensor is on and whether a sensor has malfunctioned), for example.

Some embodiments may output corrected data that may be considered raw data adjusted by one or more "correction factors." For example, as referenced herein, some detected raw data may be dependent on environmental factors, such as temperature, pressure, relative humidity, gas composition, and noise. For example, a given value of a particle count or mass may not raise a flag under normal ambient conditions, but when coupled with an elevated concentration of $CO_2$ or $O_2$ may deserve special attention/action. In other examples, the compositions of particles may be known or estimated, and only one or a few components warrant monitoring. Using the composition information along with measured particle mass, programmed computational techniques may provide levels of one or more potentially problematic components. Some correction factors are further discussed below.

Information relevant to making a decision for health and safety may also be an output in some implementations. This may include whether any exposures exceed safety limits that may be set by, for instance, OSHA or other administration or entity. These exposures may be based on instantaneous peak exposures as well as time-weighted averages. For instance, some exposures may be lower exposure limits (LEL), upper exposure limits (UEL), acute (or airborne) exposure limits (AEL), combustible limits, and short-term exposure limits (STEL), ceiling limits, or any other irregularities in sampled data that can be captured. Additionally, any quantifiable risk factors in comparison to previous historical data, trend analysis, ventilation factors, or other risk factors, depending on the environment, may be output. Such outputs may be based on data that a mobile unit has detected. In some instances, the outputs may be a prediction as to when that exposure limit may be reached in the future. For example, one output may be a notification to the wearer of a mobile monitoring unit that the wearer has not, but is expected to exceed an UEL in an additional X minutes or hours given the current and/or past detected conditions.

In some embodiments, the techniques and apparatuses described herein may output a time-weighted average (TWA) of an exposure, which indicates the average exposure to a material over a fixed time interval, such as an 8-hour workday. Some TWAs may be equal to the sum of the portion of each time period (as a decimal, such as 0.25 hour) multiplied by the levels of the substance or agent during the time period divided by the hours in the workday (e.g., 8 hours or 4 hours). Many safety regulations use TWA units, and these TWAs may provide an estimated exposure over a period of time even though measurements may not have been continuous over that entire period of time. For example, a monitoring unit may generate data for only 6.5 hours during an 8-hour period (which may be caused by a variety of reasons, such as device failure or shutdown for a period, and the monitoring unit moving outside the environment for an amount of time) and an 8-hour TWA can be calculated using the 6.5 hours of generated data. TWAs are discussed further below.

Outputs may include calculated particle information that is outside the detected range(s) provided by an air quality or particle sensor. In some implementations, an air quality sensor may provide particle counts and particle size data only for discrete particle diameters ranges or size bins, and therefore cannot directly or precisely provide data regarding particles that do not correlate directly with these discrete size bins. However, it may be desirable to provide particle count and size data for particles that are not directly measured by the sensor's size bins because, for instance, some exposure limits or regulations are in terms of these other particle sizes. The techniques and apparatuses described herein may be able to output calculated particle information, e.g., particle counts and size, for particles that are not within the discrete size bins of the sensors. For example, the air quality sensor may provide particle counts and size data for particles of 1 micron or smaller, 2 microns or smaller, and 5 microns or smaller and therefore cannot directly provide data regarding particles within these size bins, such as particles of 1.5, 3, or 4 microns or smaller. But a safety regulation may specify an exposure limit regarding particles outside these detected size bins (1, 2, and 5 microns), such as 4 microns or smaller. The techniques described herein may use the detected data for the discrete size bins, e.g., of 1, 2, and 5 microns, to determine and output calculated particle information, e.g. particle count, about particles not correlated exactly with these discrete size bins, such as particles of 4 microns or smaller. In certain embodiments, this is achieved by interpolating the data between size bins and/or by fitting the size distribution to a unimodal or multimodal lognormal size distribution.

As mentioned above, the apparatuses and techniques may determine an activity or task likely being performed near a monitoring unit, and output information related to or based on that activity. For example, using data from one or more of an accelerometer, a gyroscope, and a microphone (e.g., on a mobile monitoring unit worn by a user), a technique determines the activity that the wearer is engaged in (or that is being performed in the vicinity of the wearer) for an industrial setting. For example, as discussed herein, jackhammering may have a characteristic noise signature (as detected by a microphone on the mobile monitoring unit, as stationary monitoring unit, or both) and a characteristic motion signature. So when appropriate acoustic signals are coupled to the vibration detected from the motion sensors, e.g., the accelerometer and the gyroscope, the technique may infer that the person wearing the sensor is using a jackhammer. If, by contrast, the signal is just the noise (no associated motion detected by the inertial sensor), the technique determines that jackhammering is being done in the vicinity of the individual.

By correlating particle exposure to activity of the individual or the activity being carried out in the vicinity, an industrial hygienist or safety officer, or other individual or system can make appropriate safety or policy decisions. As discussed below, the relationship between air quality and activity may be implemented as a pre-trained model such as a machine learning model.

Alerts, alarms, and other notifications may also be outputs by the techniques and apparatuses. As mentioned above, alerts for problematic environmental conditions detected by the techniques may be provided by the notification mechanism in the form of, for example, tactile, auditory, visual, and combinations thereof. These alerts may be generated within the monitoring unit itself, at a remote site or monitoring unit (e.g., the cloud computing unit 104), or a combination. An alert may be a generic alarm and may also be a notification for a specific intervention. For example, the specific alert may be that a user should remove himself from the area, turn on engineering control, or take one or more actions. As noted above, the alert may also include a prediction about when one or more applicable exposure limits will occur.

Outputs of the techniques and apparatuses may also include instructions to local mobile and/or stationary monitoring units. These instructions may be related to hazardous or otherwise problematic environmental conditions detected or determined. For example, in response to a mobile monitoring unit detecting an exposure at or above an AEL, instructions may be issued to that mobile monitoring unit to gather additional information, such as to cause the camera to capture images, e.g., still or video, to activate a microphone to capture acoustic signals, or to activate other sensors to gather data, such as the accelerometer and gyroscope, which can be used to correlate output from sensors to activities. This gathered information may assist with diagnosing a source of exposure as well as with offering solutions and corrective actions regarding exposures. From some industrial hygiene perspectives, goals may by not only to identify if an exposure limit has been exceeded, but also what solutions may prevent that exposure in the future. This gathered information can also be used to identify particular areas and activities of high exposures and to warn and offer possible controls at these areas (limiting exposure, engineering controls, etc.).

As discussed in greater detail below, outputs may also include maps that depict detected and determined metrics, such as particle concentrations, from monitoring units in an environment. These maps may be snapshots of a single time, or a time-lapse representation of detected and determined metrics over time.

Various computational processing operations may be employed to convert input data to appropriate outputs. Examples of such operations include machine learning, application of conversion factors, and various other forms of data inversion. Suitable computational logic on the sensing unit and/or a remote computational resource is used to perform these operations.

In certain embodiments, data inversion is employed to provide particle information outside the sensed range (e.g., for particles 4 microns or smaller as mentioned above). For this purpose, examples of suitable data inversion logic include the method of moments and machine learning (e.g., artificial neural networks and Kriging). Machine learning techniques, for example, may employ a training set including data outside directed measured ranges (e.g., at 4 microns or smaller) along with data at directly measured ranges (e.g., 2.5 microns or smaller) to learn how predict results at desired points outside the directly measured ranges from data at the directly measured ranges.

Computational processing for applying correction factors, as implemented by appropriate logic, may take various forms. For example, a process may take particle count or mass readings for a particular type of particulate and convert it to a reading for a particular type of material that makes up only a fraction of materials in the particles that are directly measured. For example, if a material of interest (e.g., silica or a particular heavy metal such as cadmium) is X% of total particle mass, volume, or count, the computational process converts a direct reading of particle information (count, mass, or volume) to a reading for the material of interest. In some cases, the computational process applies a simple conversion factor. In a specific case, if silica is the compound of concern and it makes up only 15% of the mass of the particulate matter being detected, the sensed particle mass may be multiplied by 0.15 to determine the mass of silica in the sensed particles.

As an example, computational logic is configured to account for a material of interest being X% of total particle mass, volume, or count. For example, if silica is the compound of concern and it is only 15% of the mass of the particulate matter being detected, the sensed particle mass may be multiplied by 0.15 to determine the mass of silica in the sensed particles. As mentioned, appropriate conversion factors may be obtained by various techniques such as from material safety data sheets for the material under consideration. Alternatively, sample particles may be chemically analyzed. For example, previously collected samples—such as actual air sample sent to a lab—are analyzed to determine chemical composition.

In certain embodiments, the converted particle information is utilized in determining whether to trigger an alarm or other action. For example, an MSDS or other source of compositional data may indicate that a particular type of particle (generated in a particular occupational setting) has only 15% silica or other hazardous particulate content. If occupational requirements specify less than X mass of silica exposure per eight hours (e.g., 50 micrograms per $m^3$), a particle mass of X/0.15 will trigger action.

Correction factors other than those based on particle composition may be employed. Examples include corrections based on local environmental conditions; e.g., temperature, pressure, humidity, and the like. Such local conditions may, in some embodiments, be determined using sensors included in the devices described herein. Such corrections may be appropriate when operating in extreme conditions (e.g., very high temperature and humidity) and/or when the sensors are particularly sensitive changes in local conditions. The corrections may be determined by calibration, machine learning, etc.

In some cases, computational logic uses an expression that is more complicated than a simple coefficient or multiplier applied to measured values. For example, the logic may employ an expression having multiple terms and/or be non-linear. In such cases, corrective factors may be applied to a whole expression used for correction, or just one or a few terms in the expression. For example, based on instantaneous measured conditions (e.g., temperature, humidity, pressure, etc.) computational logic may adjust some coefficients or other parameters in linear or nonlinear way in the expression.

In some implementations, the processing logic is configured to account for sensor drift or other time variations in sensor behavior. Sensors such as particle counters can become less accurate because of various factors such as particulates depositing on detectors. It has been found that the level of drift due to deposition may be dependent on size and/or concentration of particles, and it may be non-linear with time; e.g., the impact of particle concentration goes as the power of 2. If a sensor's drift or degradation over time is known, the computational logic may account for this and adjust sensor output measurements accordingly. The result may be implemented as a calibration or a correction.

In some implementations, sensor drift adjustment or calibration is accomplished using two sensors on the unit and one operates only periodically and that measurement is compared to the other sensor. In another approach two sensors are used, with the one being evaluated being on a mobile unit and the other on a fixed unit; the mobile unit passes by the fixed unit and detected data is compared and accounted for. In either approach, if differences in readings from the two units vary over time, the output of the regularly used unit is adjusted to account for the difference. In certain embodiments, the logic is configured to characterize sensor health based on the reading; e.g., replace sensor if the readings are off by X amount.

In certain embodiments, the computational logic is configured to compare data against threshold/alarm conditions that are triggered using particle information in conjunction with composition data or other data about other environmental conditions. In certain embodiments, the computational logic compares directly or indirectly measured data against threshold conditions that triggers a further device action at the location of the condition. Examples of such actions include camera activation or modified operation, microphone activation, motion detection, or other local action of the unit or an associated device such as a user's phone.

In certain embodiments, computational logic is configured to generate maps of air quality in a work area or other location. The logic may be configured to generate such maps using only limited information, from one or more sensors, typically from multiple sensors. Such maps may be generated using an appropriate model such as a statistical model (e.g., produced by Kriging) or machine learning model (such as an artificial neural network). The maps are produced by interpolating air quality values (e.g., particle concentrations) or other conditions in positions between measuring unit locations (fixed and/or mobile). To provide interpolated information from data provided at only a few discrete locations, a model may be trained using data provided at many different locations beyond simply those of installed sensors in the final system. In certain embodiments, an air quality mapping routine may evolve or improve over time by using additional training data acquired by moving wearable sensors providing real time readings of particle concentration at various locations aside from the fixed monitors that might continually detect concentration at fixed locations. In some embodiments, a single model is used for calculating air quality values at all points in the interpolation space (e.g., a work area). In other embodiments, multiple separate models are used for each of multiple interpolation positions.

Figure 7:
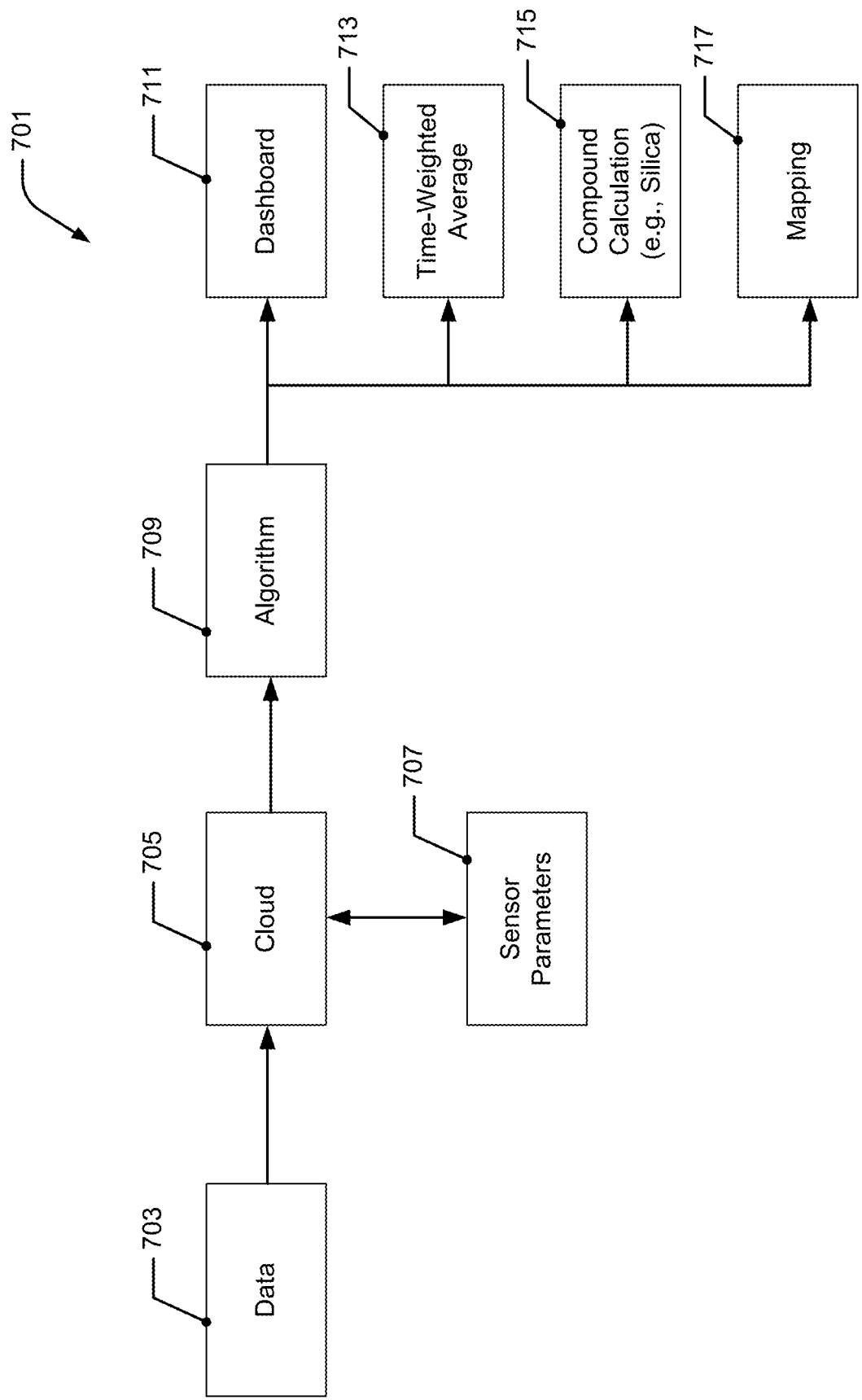
FIG. 7 depicts a computational framework for implementation various analyses as described herein.

FIG. 7 presents an example of an architecture for a system 701 that provides computational resources for one or more monitoring units. In this example, most or all of the relevant computing and/or data storage is provided remotely, e.g. on the cloud as indicated by block 705. Data 703, which includes at least some data from a local monitoring unit, typically including a mobile monitoring unit, is provided to remote processing and/or storage resources such as cloud 705. Other information such as sensor parameters (shown in block 707) may also be provided to or stored on the remote processing resources. Sensor parameters may include any of various types of information about the remote sensors and may be useful in interpreting sensor data 703 and/or generating accurate outputs from processing algorithms. Examples of sensor parameters include correction factors particular sensors, conversion information for determining concentrations of particular components of sensed particles, parameters for reconfiguring operation of the monitoring units, etc. Using the data 703 and optionally sensor parameters 707, one or more algorithms 709 may provide one or more outputs. As examples, algorithms 709 may include statistical models, machine learning models, regression models, classification trees, random forest models, simple expressions (linear or non-linear), look up tables, and the like. In the depicted embodiments, processing logic for implementing algorithm(s) 709 includes instructions for implementing any one or more of a dashboard 711, time-weighted average values 713 of particle counts or other local conditions, material or compound (e.g., silica mass per unit volume of air) concentration values 715, and location mapping 717 (e.g., air quality maps for particular locations of provided data 703).

User Interfaces

The data generated and information determined by one or more monitoring units and/or the remote computing unit may be presented in various manners. In some instances, data and information may be presented on the monitoring unit itself, similar to described above. Referring back to FIG. 1, this data and information may be presented via the notification mechanism 174 and, referring back to FIGS. 4A and 4B, via the display 446. For example, the display 446 of a mobile monitoring unit 402 may display particle size, particle counts, particle mass concentration, size distribution, volume concentration, size distribution, particle composition/type, time weighted averages, exposure risk factors, safety risk factors, real time mapping, geolocation data, and time. Additionally, data and information presented to a wearer may include an alert or alarm, such as flashing lights and sounds.

Figure 8:
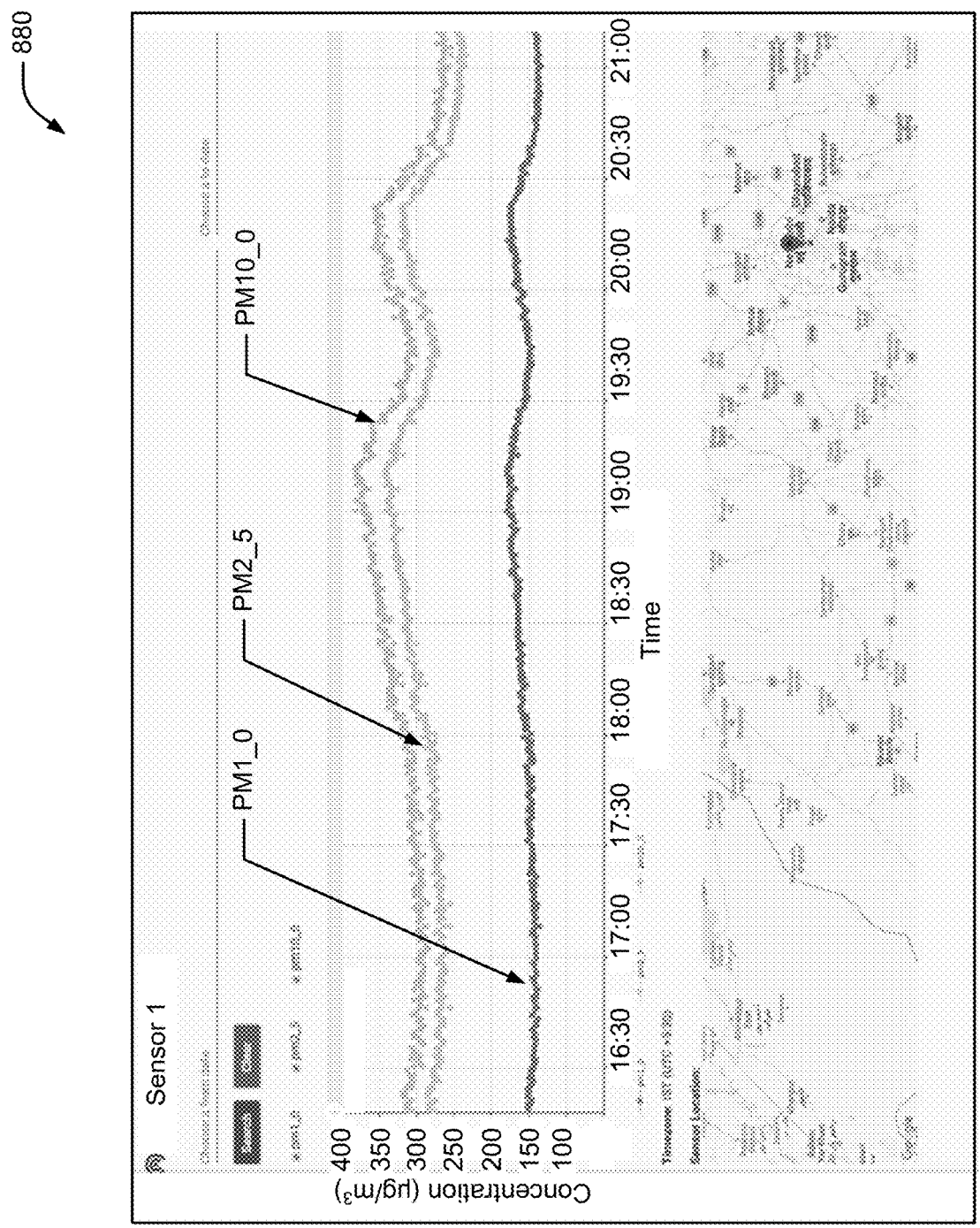
FIG. 8 depicts a first example dashboard.

The generated data by one or more monitoring units and determined information may also be displayed in a dashboard on an electronic device, such as a computer, laptop, table, smart phone, and the like. The dashboard may include any of the data measured and information determined as described above. For example, FIG. 8 depicts a first example dashboard. The dashboard 880 includes a graph which displays detected particulate concentrations, in micrograms per meter cubed ($\mu g/m^3$), over time for three different size bins of particles, PM1.0, PM2.5 and PM10.0. As can be seen, the detected particulate concentrations for each size bin changes over time, with a maximum peak between time 19:00 and 19:30, and another increase between time 20:00 and 20:30. The dashboard 880 also includes a map showing the geographical location of the monitoring unit in real time and historically.

The dashboard may be interactive such that a user can select and access historical and real-time data of mobile monitoring units and stationary units. For example, the dashboard may allow a user may to select a historical location of a mobile monitoring unit and then display the data and information that were generated and determined for that location. Referring to FIG. 8, the data in the chart may be the data generated by a monitoring unit at the location depicted in the map.

Figure 9:
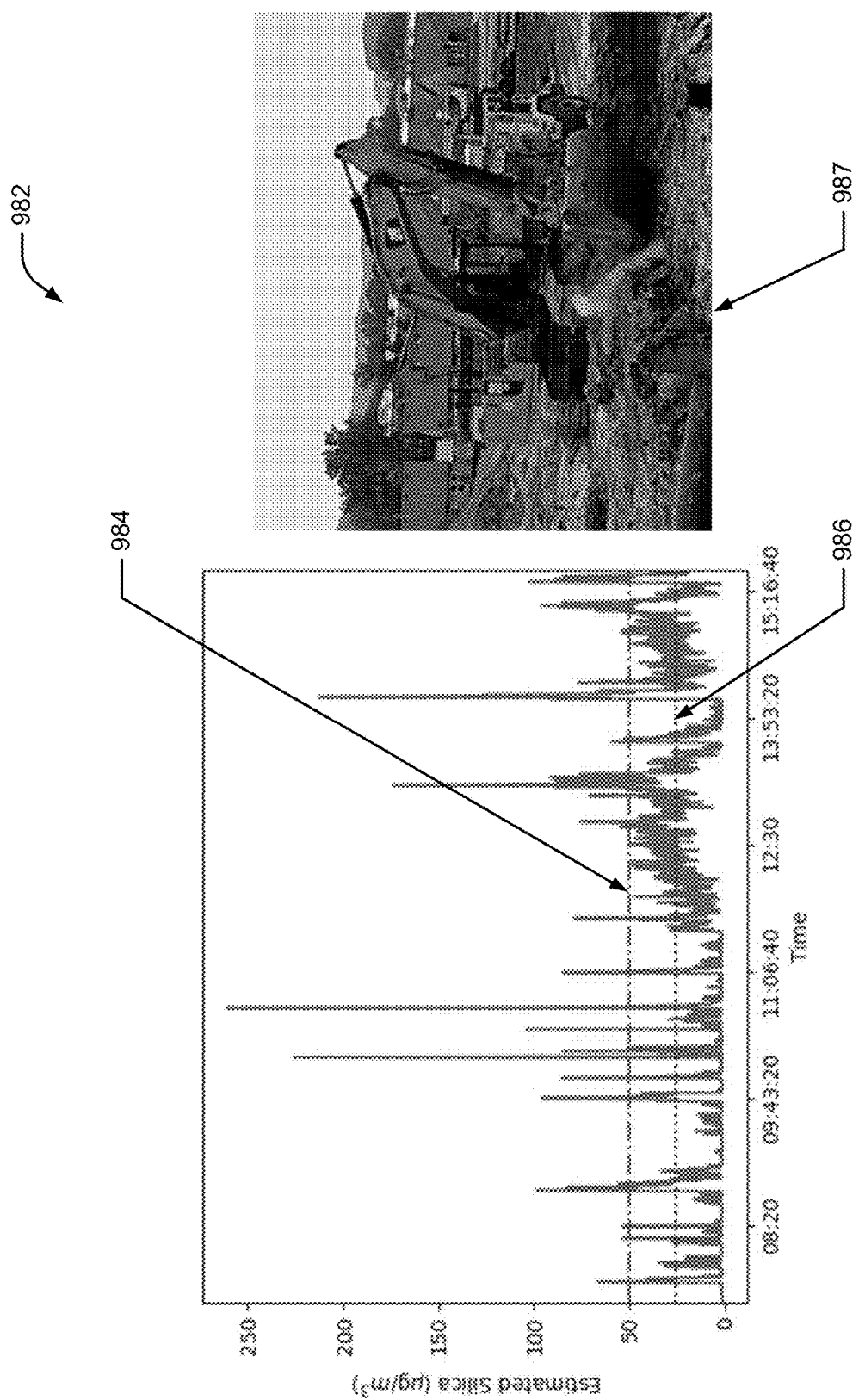
FIG. 9 depicts a second example dashboard.

The dashboard may also display time-weighted average information. In certain embodiments, the image/video taken by a camera as directed by sensor output maybe displayed on the dashboard along with the sensor output relevant to the image. See item 987 in FIG. 9. FIG. 9 depicts a second example dashboard; here, the chart depicts estimated silica measurements made by a mobile monitoring unit worn by a user over time, approximately 8 hours. The mobile monitoring unit may use the air quality sensor 108 described above to detect total respirable dust over a time period and a correction factor may be applied to determine the estimated amount of silica within the detected respirable dust. In this instance, as indicated in FIG. 9, it is assumed the respirable dust contains 32.6% to 40% of silica (this may be obtained by a material safety data sheet (MSDS) for that respirable dust stored in or accessible by the cloud computing unit). The detected respirable dust can then be adjusted using this assumption in order to obtain the estimated silica, in micrograms per meters cubed, over the time period. The data shown in the chart represents that estimated silica, which is the measured respirable dust data adjusted by the assumed silica percentage of that respirable dust.

As noted above, the measured data may be used to determine the time-weighted average (TWA) which indicates the average exposure to a material over a fixed time interval, such as an 8-hour workday. In FIG. 9, the eight hour time weighted average (TWA) was obtained for the measured respirable dust, which is 58.13 $\mu g/m^3$. Because it is assumed that the measured respirable dust contains an assumed silica percentage of 32.6 to 40, the measured respirable dust is multiplied by this percentage to determine an estimated silica TWA, which is 18.95 to 23.25 $\mu g/m^3$.

The second example dashboard 982 may also include level thresholds of detected exposures, such as permissible exposure limits and action levels. For instance, FIG. 9 includes a permissible exposure limit line 984 which may indicates the permissible amount of exposure for silica, which is illustrated as 50 $\mu g/m^3$. Although the estimated silica 8-hour TWA (18.95 to 23.25 micrograms per meter cubed) is below this threshold, dashboard 982 shows that the mobile monitoring unit detected numerous short-term exposures that were higher than this threshold, such as between times 9:43:20 and 11:06. Determining specific instances higher than the permissible exposure limits is advantageous for monitoring and taking corrective actions to improve health and safety of an environment. For instance, if these exposures were determined for a jackhammer operator, these instances can be used to assess which work conditions may have caused these exposures and to take corrective action to prevent or stop these exposures, such as using different safety measures in these conditions in the future, as well as issuing real-time warnings to the user during these exposures.

Similarly, another level threshold may be an action level threshold which indicates when an action should be taken with respect to the exposure. FIG. 9 includes action level threshold 986 which represents the level at which an action should be taken based on the detected conditions. These actions can include, for instance, instituting additional monitoring, turning on or installing engineering or safety controls, issuing a notification (e.g., that exposures are above a particular level), and the like. The action level threshold may also be below the exposure limit threshold in order to prevent the exposure limit threshold from being reached.

Figure 10:
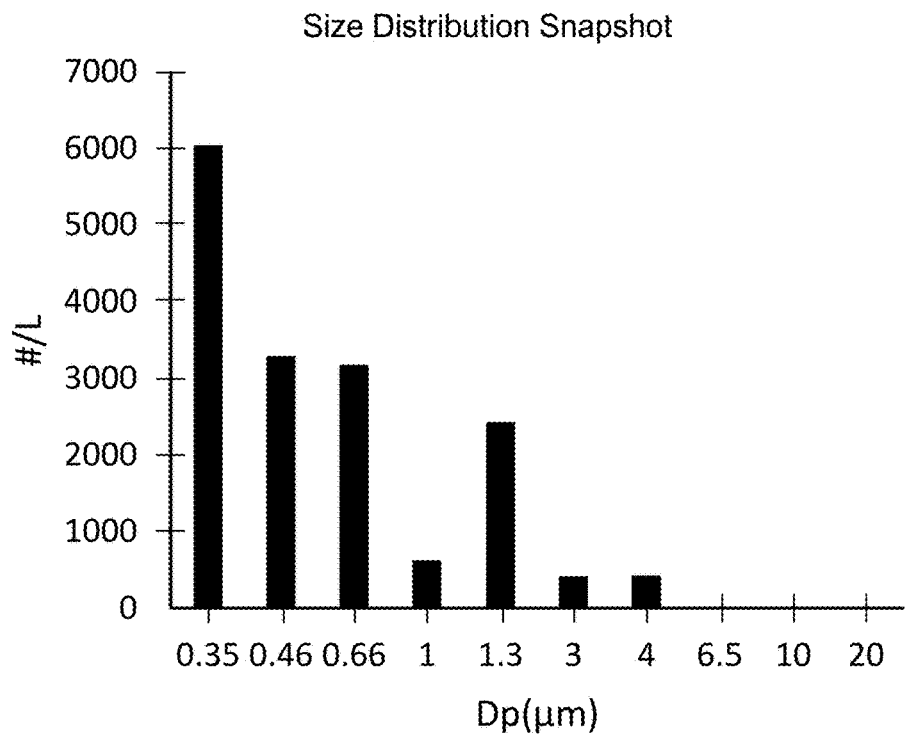
FIG. 10 depicts a histogram of a size distribution snapshot for the air quality sensor of a monitoring unit.
Figure 11:
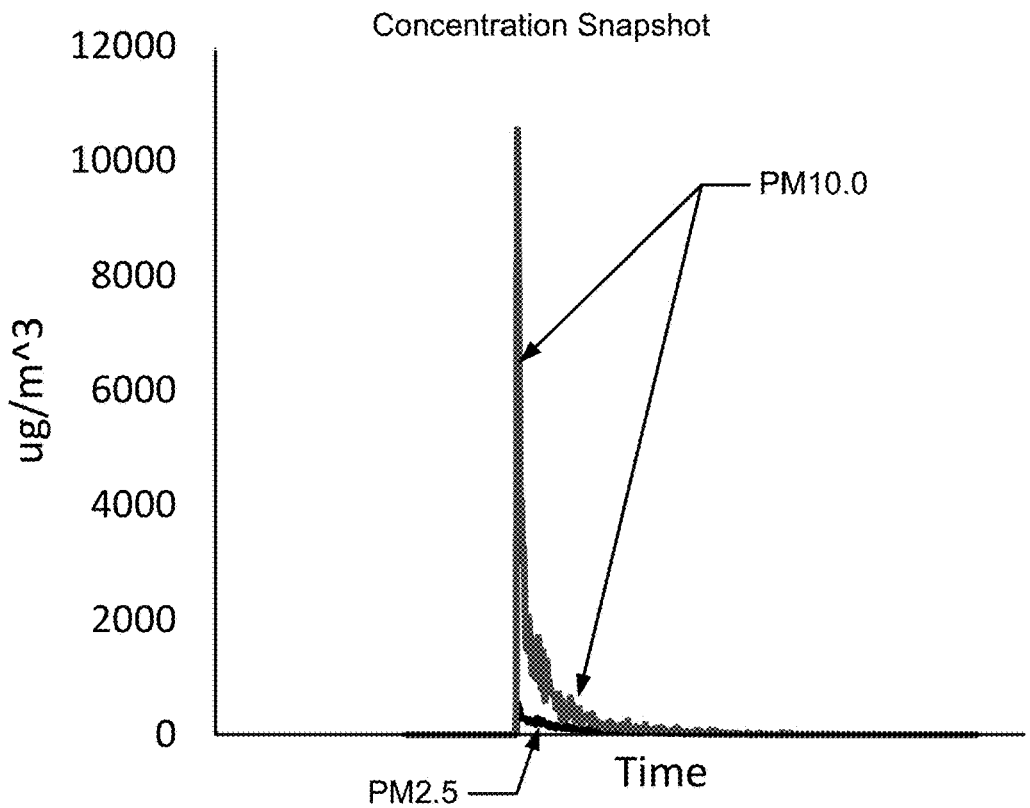
FIG. 11 depicts a concentration snapshot of detected particles of different sizes over a time period.

The dashboard may also present real-time concentration and size distributions. FIG. 10 depicts a histogram of a size distribution snapshot for the air quality sensor of a monitoring unit. Here, the vertical axis shows the number of particles per liter and the horizontal axis shows the diameter of the particle, in micrometers ($\mu m$). The time or time period which is depicted can vary. In some embodiments, the "snapshot" may be the measurements at a specific time or may be an average of the readings over a time period. For example, the air quality sensor may take measurements every 500 milliseconds and the snapshot may be the average of those measurements over 1 second, or 5 seconds. In FIG. 10, the numbers per liter (#/L) of detected particles of various sizes is seen. For instance, 6,000 particles per liter of particles having a diameter of 0.35 $\mu m$ has been detected, and approximately 750 particles per liter of particles having a diameter of 1.3 $\mu m$ has also been detected. Similarly, FIG. 11 depicts a concentration snapshot of detected particles of different sizes over a time period. Here, two particle masses are seen, PM10.0 and PM2.5, and over this illustrated time period, the concentration of particles with mass PM10.0 was much higher than the concentration of particles of mass PM2.5.

In some embodiments, the dashboard may also present a map that illustrates concentrations of one or more metrics within a particular area or environment. These metrics may be any measured or determined item described herein, such as particulate matter, specific particles and compounds, e.g., silica or carbon monoxide, temperature, sound, and relative humidity. In some implementations, the graphical representation may look similar to a heat map with differently colored or shaded gradients indicating different concentrations levels of the one or more metric(s). The map's graphical representations may be generated using the above techniques, such as interpolations of data generated by sensor readings. In some of these embodiments, measurements of one or more environmental conditions are taken at specific, known locations and values of the one or more metrics in between these locations may be interpolated. For example, a plurality of monitoring units may measure environmental conditions that include particulate matter, temperature, pressure, and relative humidity at a plurality of known locations within an environment, and the levels of a metric, such as particulate matter, may be determined at those known locations and in-between those known locations using the techniques described above. The plurality of monitoring units may be communicatively connected with each other, like in FIG. 3, and may also be communicatively connected with the cloud computing unit which may perform some or all of the interpolations and techniques described herein.

Figure 12:
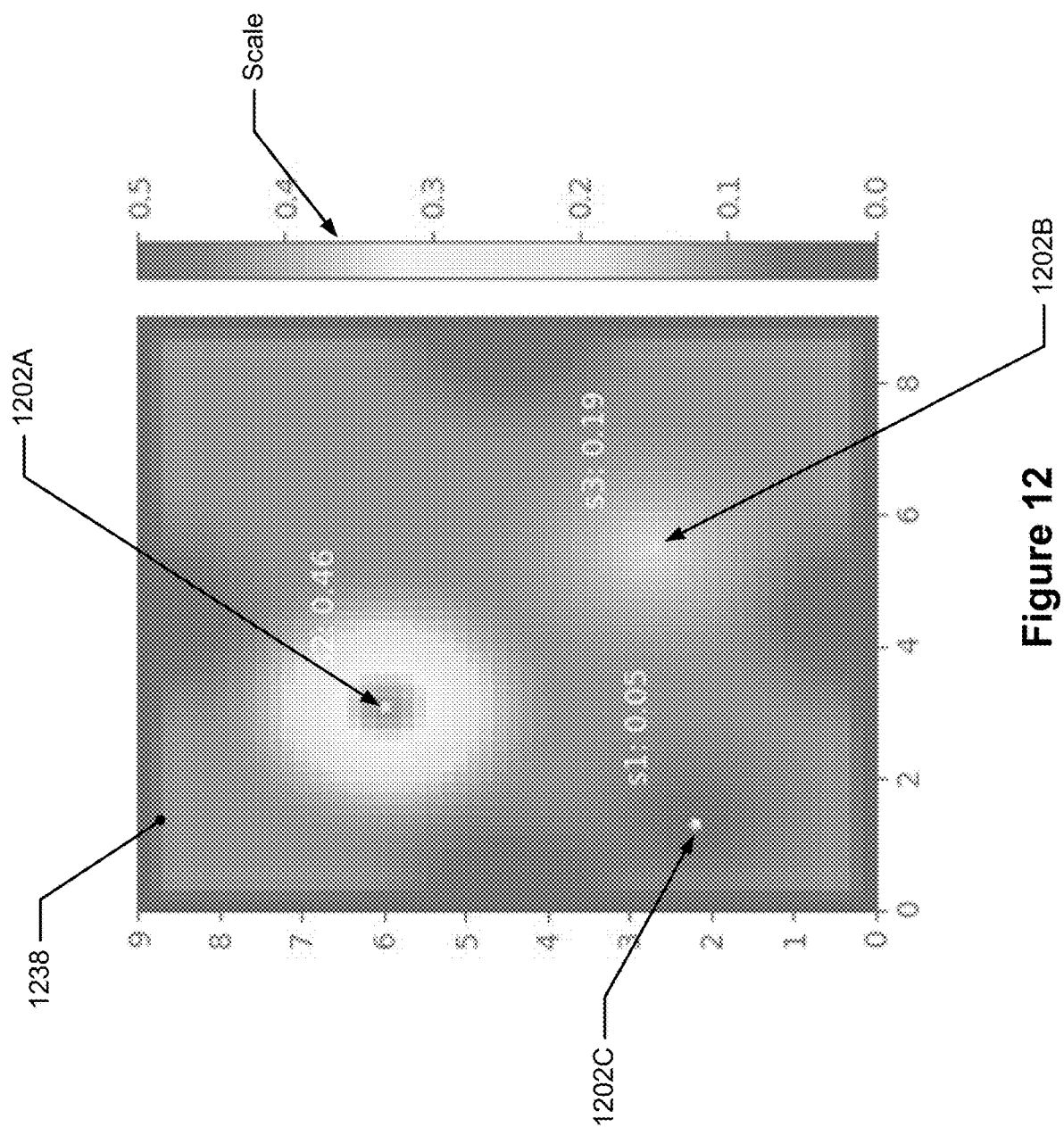
FIG. 12 depicts an example dashboard map.

FIG. 12 depicts an example dashboard map. Here, the depicted environment 1238 is a rectangular room which includes multiple monitoring units 1202A-1202C, represented as stars, positioned throughout the environment 1238. The levels of a metric, based on the data gathered by the sensors of each monitoring units 1202A-1202C, is graphically represented in the room according to the vertical gradient scale on the right; higher levels of the metric are generally indicated in lighter color while lower levels are generally depicted as darker. As can be seen, the highest levels of the metric are around the monitoring unit 1202A (0.46 generic measurement units (GMU)), with the next highest levels around monitoring unit 1202B (0.19 GMU), and with lowest level around monitoring unit 1202C (0.05 GMU). As stated above, each monitoring unit measures one or more environmental conditions at its location and the metric is determined at and in between those known locations using techniques described above.

Based on the displayed information in FIG. 12, it may be inferred that an event occurred around monitoring unit 1202A which caused the highest levels of the metric to occur at that general location in the environment. For example, each of the monitoring units 1202A-120CH may have air quality sensors 1208 configured to detect and count particulate matter, as described above, and the metric depicted in FIG. 12 may be detected and interpolated particulate matter. In this example, the particulate matter is highest around monitoring unit 1202A and lowest around monitoring unit 1202C.

Figure 13A:
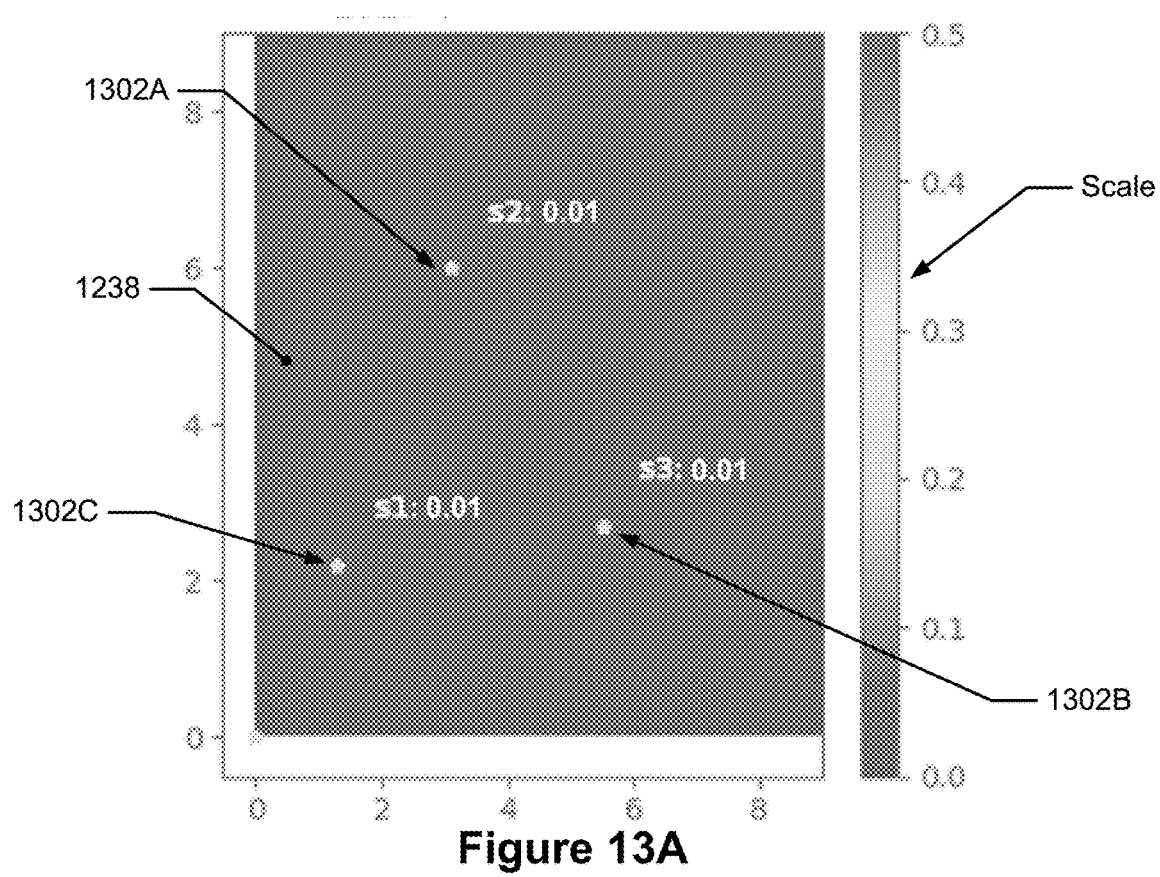
FIGS. 13A-13C depicts an example map sequence.
Figure 13B:
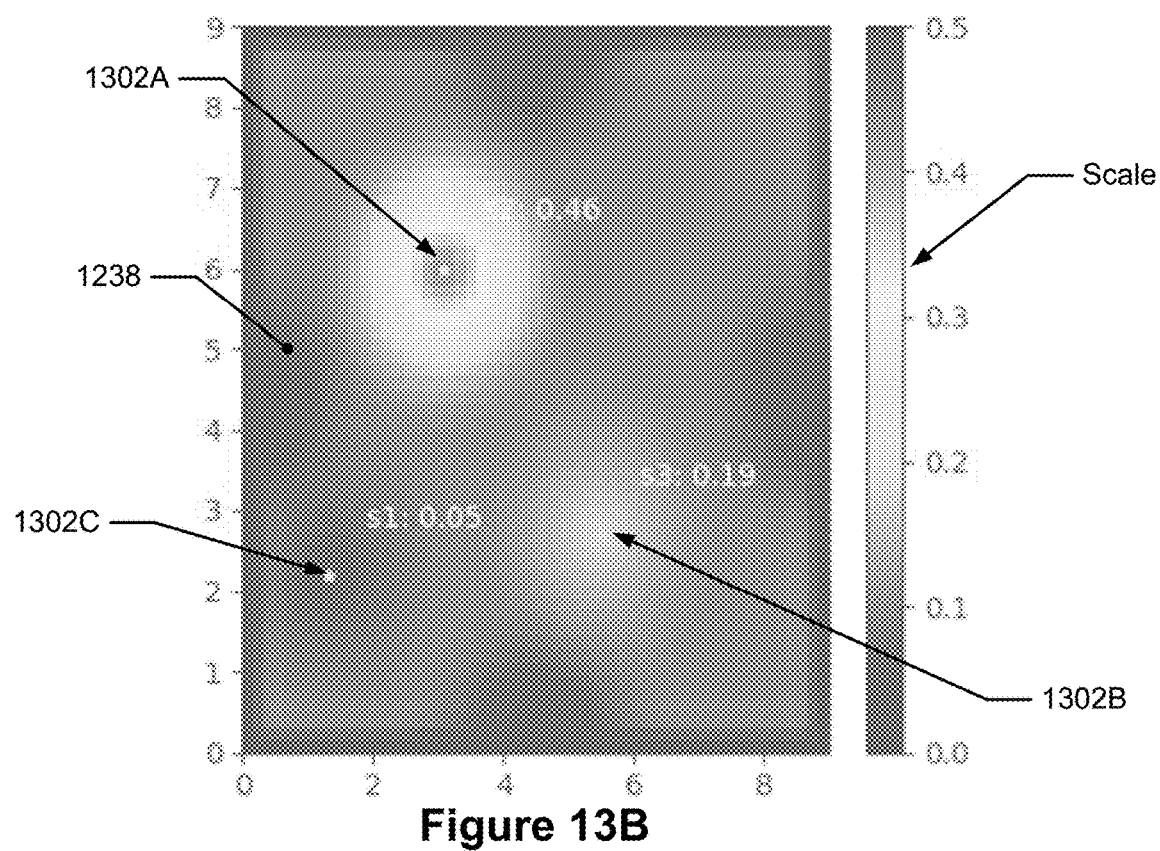
Figure 13C:
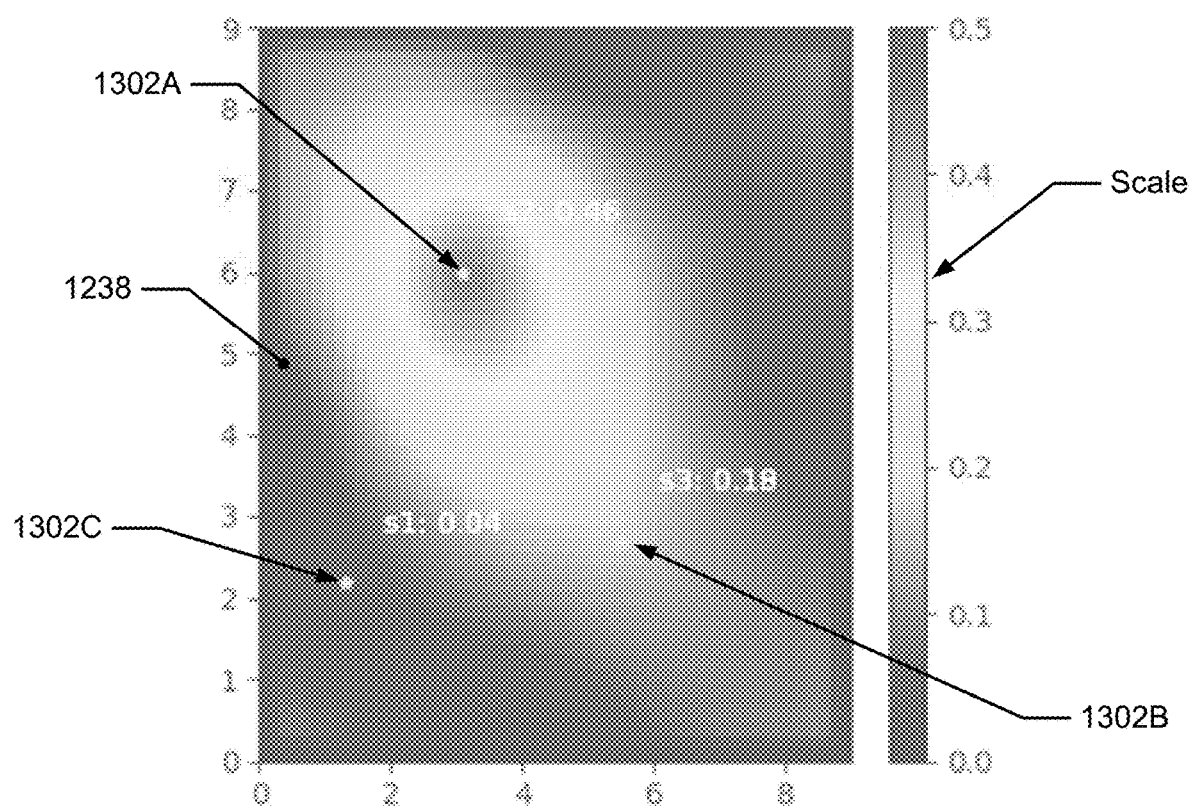

In some instances, the dashboard map may provide a snapshot at a particular time. In some other instances, the dashboard map may illustrate a sequence of a metric's levels within an environment over a period of time. FIGS. 13A-13C depict an example map sequence. Similar to FIG. 12, the depicted environment 1338 in FIGS. 13A-13C is a rectangular room which includes multiple monitoring units 1302A-1302C, represented as stars, positioned throughout the environment 1338. Again, like with FIG. 12, the levels of a metric, based on the data gathered by the sensors of each monitoring units 1302A-C, is graphically represented in the room according to the vertical gradient scale on the right; higher levels of the metric are generally indicated in lighter color while lower levels are generally depicted as darker.

Each of FIGS. 13A-13C may be considered a snapshot of the metric at different sequential times. In FIG. 13A, the first in the sequence at time 1, all the monitoring units 1302A-C are reading negligible levels, about 0.01 GMU at each unit. In the second sequence of FIG. 13B, an event has occurred in which a metric's levels have increased in the depicted environment 1338. As can be seen, the highest levels of the metric are seen around monitoring unit 1302A, about 0.46 GMU, with the next highest level around monitoring unit 1302B, about 0.19 GMU, and the lowest levels around monitoring unit 1302C, about 0.05 GMU.

In FIG. 13C, the levels of the metric detected by monitoring units 1302A and 1302B have remained the same, the have the levels around monitoring unit 1302A has increased and grown in size. Between these two Figures, the levels of the metric indicate that the metric has moved within environment 1338 and also increased in level. This sequence illustrates how differing levels of a metric within an environment over time can be illustrated by a dashboard. The dashboards are not limited to a schematic of a room, but can also illustrate concentrations using other representations, such as a geographical map. In FIGS. 13A-13C, a particulate generating event occurred around monitoring unit 1302A and these Figures illustrate the movement and increase of particulates within the environment 1338.

Additionally, as described above, the depicted concentrations or levels of a metric may also be based on monitoring units that are moving, stationary, or both. The examples of FIGS. 12 and 13A-C depict stationary monitoring units, but the same illustrations may utilize mobile monitoring units as well. Based on the known locations of the monitoring units, whether they are stationary or mobile, the values of metrics between these locations can be interpreted and graphically represented on a map. In some such examples, the map may also indicate the various locations or paths of the monitoring units while is some other examples, the map may not include the locations of any of the monitoring units.

As mentioned above, the data gathered by monitoring units and outputs described herein can be used for industrial hygiene reports. In some instances, the dashboards may display the information for some industrial hygiene reports. These reports can include, for example, end of shift analysis such as total TWA and silica TWA; instantaneous and acute exposure analysis during the shift and associated images/videos pertaining to the instantaneous exposure; risk factors determined by the data gathered including the exposure data, the activity data, and the image data; information on the sampling time (start time, end time); task or activity; influencing factors; process parameters; surrounding environments; specific events during the sampling period; objective data; insights regarding the root cause of the exposures; suggestions for effective remediation measures; and exposure levels.

Example Applications

The apparatuses and techniques described herein can be used for numerous applications. For instance, these apparatuses and techniques assist with safety in a variety of occupations, such as mining, construction, agricultural, pharmaceutical, industrial, manufacturing, firefighting, and the like. In these occupations, an individual worker's instantaneous, real-time, and TWA exposures to various hazardous materials, such as coal, silica, lead, chromium (VI), hazardous aerosols, gases, volatile organics, CO, $CO_2$, Ozone, $SO_2$, NOX, VOC, HCN, methane, radon, radioactive particles, and other potentially hazardous materials such as those identified in the American Conference of Governmental Industrial Hygienists (ACGIH) Threshold Limit Values /Biological Exposure Indices (TLVs/BEIs) tables, may be determined using mobile monitoring devices worn by the workers and positioned within occupational locations, such as within a mine, around a construction site or refinery, and within a manufacturing plant. This may allow for real-time monitoring of a worker's exposure to hazardous materials, for alerts or alarms to be issued to a worker, manager, or safety personnel, and for corrective actions to be taken such as instituting more monitoring, increasing or decreasing engineering controls such as fans or filters to remove the hazardous materials from an area. It may also be used to determine when worker must be wearing PPE and when it is safe to remove PPE. It may also be used to determine safe return of worker to a process area after a hazardous process has completed and it is safe for workers to enter the area.

These apparatuses and techniques may also be useful to public health and safety. For example, these monitoring units may be positioned around and worn by people in cities, homes, and municipalities for the monitoring and detection of harmful and hazardous materials. This may include detecting and determining city-wide pollutants from automobiles, and area wide particulates and hazardous materials produced by a fire. This may also include monitoring and determining an area's risk assessment COPD, asthma, and other health conditions.

The apparatus and techniques described herein may also be used to control the ventilation in a building effectively. In this case the system output may be used to drive a control to change ventilation rates in a building or mine or any enclosed environment.

The apparatus and techniques described herein may be used for early detection of equipment failure, infrastructure failure, or hazard. For example, small particle detection/VOC detection in a data center may be an early indication of a fire.

Unless the context of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein. The term "substantially" herein, unless otherwise specified, means within 5% of the referenced value. For example, substantially perpendicular means within +/−5% of parallel.

In certain embodiments, the systems and methods described herein are configured to track a person's location as either indoors or outdoors. In certain embodiments, the systems and methods described herein are configured to determine if the indoor environment is air-conditioned or not. This may be based on RSSI data from cellular systems and/or GPS data, along with temperature, humidity data and/or and their changes. A person entering indoor may see a drop in cellular and GPS RSSI. Using temperature and humidity changes linked to the above changes, the air conditioning of the indoor environment maybe detected. In some cases, a camera may further be used to make the indoor/outdoor determination using image recognition.

In some applications, the ability to monitor noise exposures experienced by an individual or at a given location is determined using acoustic signals captured using the microphone. The logic for detecting noise exposure may implement various metrics, triggers, outputs, etc. in manners similar to the particle exposure embodiments described above.

What is claimed is:

1. A system comprising:
 a monitoring unit positioned within an environment and that includes:
  an air quality sensor configured to generate particle data regarding particles in the environment,
  a temperature sensor configured to generate temperature data,
  a pressure sensor configured to generate pressure data,
  a relative humidity sensor configured to generate pressure data,
  a first communications unit with an antenna configured to transmit data between the monitoring unit and, directly or indirectly, a remote computing unit, and
  a controller comprising one or more first processors and one or more first non-transitory memory devices that store instructions for controlling the one or more first processors to:
   cause the air quality sensor to generate particle data about particles in the environment,
   cause the air temperature sensor to generate temperature data,
   cause the air pressure sensor to generate pressure data,
   cause the relative humidity sensor to generate humidity data, and
   transmit, using the first communications unit, the temperature data, pressure data, and humidity data to the remote computing unit, and
   transmit, using the first communications unit, the particle data generated by the air quality sensor to the remote computing unit; and
 the remote computing unit positioned outside the environment and containing one or more second processors, one or more second communications unit, and one or more second non-transitory memory devices that stores instructions for controlling the one or more second processors to:
  receive and store the particle data,
  receive and store the temperature data, the pressure data, and the humidity data,
  determine, based on the received particle data generated by the air quality sensor, whether a first exposure threshold has been exceeded for the monitoring unit,
  determine, based on the received particle data, temperature data, pressure data, and the humidity data, first adjusted particle information, and
  determine, based on the first adjusted particle information, whether the first exposure threshold has been exceeded.

2. The system of claim 1, wherein the first communications unit and controller are configured as a single unit.

3. The system of claim 1, further comprising a notification mechanism configured to present a person with a notification related to the particle data, wherein:
 the one or more second non-transitory memory devices of the remote computing unit stores further instructions for controlling the one or more second processors to cause, based on the particle data, the notification mechanism to present the person with the notification related to the particle data.

4. The system of claim 1, wherein:
 the one or more second non-transitory memory devices of the remote computing unit further stores environmental data about the environment, and
 the one or more second non-transitory memory devices of the remote computing unit stores further instructions for controlling the one or more second processors to:
  access the environmental data,
  determine, based on the received particle data and the environmental data, second adjusted particle information, and
  determine, based on the second adjusted particle information, whether the first exposure threshold has been exceeded.

5. The system of claim 4, wherein the environmental data comprises one or more of: material safety data sheet (MSDS) data, weather data, historical detected particle data, data generated by another monitoring unit in the environment, data regarding activity being performed in the environment, and public data.

6. The system of claim 1, further comprising:
a second monitoring unit positioned within the environment and that includes:
  a second air quality sensor configured to generate data regarding particles in the environment,
  a third communications unit with an antenna configured to transmit data between the second monitoring unit and the remote computing unit, and
  a second controller comprising one or more third processors and one or more third non-transitory memory devices that store instructions for controlling the one or more third processors to:
    cause the second air quality sensor to generate second particle data about particles in the environment, and
    transmit, using the third communications unit, the second particle data generated by the air quality sensor to the remote computing unit,
wherein:
  the first communications unit is further configured to transmit data between the second monitoring unit, and
  the one or more second non-transitory memory devices of the remote computing unit stores further instructions for controlling the one or more second processors to:
    receive and store the second particle data, and
    determine, based on the received second particle data, whether the first exposure threshold has been exceeded for the second monitoring unit.

7. The system of claim 6, wherein the one or more second non-transitory memory devices of the remote computing unit stores further instructions for controlling the one or more second processors to:
  determine, based on the received particle data and the second particle data, whether the particle data is offset from the second particle data by a first offset.

8. The system of claim 6, wherein:
the monitoring unit is a mobile monitoring unit configured to be moved within the environment, and
the second monitoring unit is a stationary monitory unit in a fixed position within the environment.

9. The system of claim 6, wherein the monitoring unit and the second monitoring unit are mobile monitoring units configured to be moved within the environment.

10. The system of claim 6, wherein the one or more second non-transitory memory devices of the remote computing unit stores further instructions for controlling the one or more second processors to:
  determine, based on the received particle data and the second particle data, whether the first exposure threshold has been exceeded for the monitoring unit.

11. The system of claim 1, wherein the first exposure threshold comprises a time-weighted average, an acute exposure limit, an upper exposure limit, a lower exposure limit, a combustible limit, and a short-term exposure limit.

12. The system of claim 1, wherein:
the monitoring unit further comprises an accelerometer, a gyroscope, and a microphone,
the one or more first non-transitory memory devices stores further instructions for controlling the one or more first processors to:
  cause the accelerometer to generate accelerometer data, the gyroscope to generate gyroscopic data, and the microphone to generate sound data, and
  transmit, using the first communications unit, the accelerometer data, gyroscopic data, and sound data, to the remote computing unit, and
the one or more second non-transitory memory devices stores further instructions for controlling the one or more second processors to determine, based on the accelerometer data, gyroscopic data, and sound data, an activity being performed within a first distance from the monitoring unit.

13. The system of claim 12, wherein the one or more second non-transitory memory devices stores further instructions for controlling the one or more second processors to determine, based on the accelerometer data, gyroscopic data, and sound data, whether a wearer of the monitoring unit is performing an activity.

14. A monitoring unit comprising:
a case with an inlet and an outlet;
an air quality sensor fluidically connected to the inlet and the outlet, and configured to generate particle data regarding particles in air drawn through the inlet;
an accelerometer;
a gyroscope;
a microphone;
a camera;
a communications unit with an antenna configured to transmit data between the monitoring unit and a remote computing unit; and
a controller comprising one or more processors and one or more non-transitory memory devices, wherein:
  the case encompasses the air quality sensor, the communications unit, and the controller, and
  the one or more non-transitory memory devices store instructions for controlling the one or more processors to:
    cause the air quality sensor to generate particle data about particles in air drawn through the inlet,
    cause the accelerometer to generate accelerometer data,
    cause the gyroscope sensor to generate gyroscopic data,
    cause the microphone to generate sound data,
    cause the camera to generate imaging data,
    transmit, using the communications unit, the data generated by the air quality sensor to the remote computing unit, and
    transmit, using the communications unit, the accelerometer data, gyroscopic data, sound data, and imaging data to the remote computing unit.

15. The monitoring unit of claim 14, further comprising a notification mechanism configured to present a person with a notification related to the particle data, wherein:
  the one or more non-transitory memory devices stores further instructions for controlling the one or more processors to cause, based on the particle data, the notification mechanism to present the person with the notification related to the particle data.

16. The monitoring unit of claim 15, wherein the notification mechanism includes a display on the case that is configured to present the notification to the person.

17. The monitoring unit of claim 15, wherein the one or more non-transitory memory devices stores further instructions for controlling the one or more processors to:
  receive a remote instruction from the remote computing unit, and cause, based on the remote instruction received from the remote computing unit, the notification mechanism to present the person with the notification related to the particle data.

18. The monitoring unit of claim 15, wherein the notification is one or more of alarm, alert, message, an auditory output, an electronic communication, an electromagnetic communication, a visual output, and a tactile output.

19. The monitoring unit of claim 14, further comprising:
a temperature sensor;
a pressure sensor; and
a relative humidity sensor, wherein the one or more non-transitory memory devices stores further instructions for controlling the one or more processors to:
cause the air temperature sensor to generate temperature data,
cause the air pressure sensor to generate pressure data,
cause the relative humidity sensor to generate humidity data, and
transmit, using the communications unit, the temperature data, pressure data, and humidity data to the remote computing unit.

20. The monitoring unit of claim 14, wherein:
the communications unit is further configured to gather position data about a position of the monitoring unit within an environment, and
the one or more non-transitory memory devices stores further instructions for controlling the one or more processors to:
cause the communications unit is further configured to gather position data about the position of the monitoring unit within an environment, and
transmit the position data to the remote computing unit.

21. The monitoring unit of claim 14, further comprising a second air quality sensor fluidically connected to the inlet and the outlet, and configured to generate second particle data regarding particles in air drawn through the inlet, wherein:
the one or more non-transitory memory devices stores further instructions for controlling the one or more processors to:
cause the second air quality sensor to generate second particle data about particles in air drawn through the inlet,
determine, based on the particle data and the second particle data, whether the particle data is offset from the second particle data by a first offset, and
transmit information related to the determination of the first offset to the remote computing unit.

22. The monitoring unit of claim 14, further comprising wearable features that are configured to enable the monitoring unit to be worn by a person within that person's breathing zone.

23. A method for monitoring conditions of an environment, the method comprising:
generating, using an air quality sensor on a monitoring unit positioned within an environment, particle data regarding particles in the environment;
transmitting the particle data from the monitoring unit to a remote computing unit outside the environment;
determining, based on the particle data generated by the air quality sensor, whether a first threshold has been exceeded;
generating, using an accelerometer, a gyroscope, and a microphone on the monitoring unit, accelerometer data, gyroscopic data, and sound data, respectively;
transmitting the accelerometer data, gyroscopic data, and sound data from the monitoring unit to the remote computing unit; and
determining, based on accelerometer data, gyroscopic data, and sound data, whether an activity is being performed within a first distance of the monitoring unit.

24. The method of claim 23, wherein the transmitting is performed simultaneously with the generating.

25. The method of claim 23, wherein the determining is at least partially performed on the remote computing unit.

26. The method of claim 23, further comprising:
generating, using a temperature sensor, a pressure sensor, and a relative humidity sensor on the monitoring unit, temperature data, pressure data, and humidity data, respectively;
transmitting the temperature data, pressure data, and humidity data from the monitoring unit to the remote computing unit;
determining, based on the particle data, temperature data, pressure data, and humidity data, adjusted particle information; and
determining, based on the adjusted particle information, and whether the first threshold has been exceeded.

27. The method of claim 23, further comprising determining, based on accelerometer data, gyroscopic data, and sound data, whether the activity is being performed by a wearer of the monitoring unit.

28. The method of claim 23, further comprising:
generating, based on one or more of accelerometer data, gyroscopic data, and sound data, imaging data using a camera on the monitoring unit; and
transmitting the imaging data from the monitoring unit to the remote computing unit.

29. A system comprising:
a monitoring unit positioned within an environment and that includes:
an air quality sensor configured to generate particle data regarding particles in the environment,
a first communications unit with an antenna configured to transmit data between the monitoring unit and, directly or indirectly, a remote computing unit, and
a controller comprising one or more first processors and one or more first non-transitory memory devices that store instructions for controlling the one or more first processors to:
cause the air quality sensor to generate particle data about particles in the environment, and
transmit, using the first communications unit, the particle data generated by the air quality sensor to the remote computing unit; and
the remote computing unit positioned outside the environment and containing one or more second processors, one or more second communications unit, and one or more second non-transitory memory devices that stores environmental data about the environment, and that stores instructions for controlling the one or more second processors to:
access the environmental data,
determine, based on the received particle data and the environmental data, second adjusted particle information,
receive and store the particle data,
determine, based on the received particle data generated by the air quality sensor, whether a first exposure threshold has been exceeded for the monitoring unit, and determine, based on the second adjusted particle information, whether the first exposure threshold has been exceeded.

30. The system of claim 29, wherein the first communications unit and controller are configured as a single unit.

31. The system of claim 29, further comprising a notification mechanism configured to present a person with a notification related to the particle data, wherein:
the one or more second non-transitory memory devices of the remote computing unit stores further instructions for controlling the one or more second processors to cause, based on the particle data, the notification mechanism to present the person with the notification related to the particle data.

32. The system of claim 29, wherein the environmental data comprises one or more of: material safety data sheet (MSDS) data, weather data, historical detected particle data, data generated by another monitoring unit in the environment, data regarding activity being performed in the environment, and public data.

33. The system of claim 29, further comprising:
a second monitoring unit positioned within the environment and that includes:
a second air quality sensor configured to generate data regarding particles in the environment,
a third communications unit with an antenna configured to transmit data between the second monitoring unit and the remote computing unit, and
a second controller comprising one or more third processors and one or more third non-transitory memory devices that store instructions for controlling the one or more third processors to:
cause the second air quality sensor to generate second particle data about particles in the environment, and
transmit, using the third communications unit, the second particle data generated by the air quality sensor to the remote computing unit,
wherein:
the first communications unit is further configured to transmit data between the second monitoring unit, and
the one or more second non-transitory memory devices of the remote computing unit stores further instructions for controlling the one or more second processors to:
receive and store the second particle data, and
determine, based on the received second particle data, whether the first exposure threshold has been exceeded for the second monitoring unit.

34. The system of claim 33, wherein the one or more second non-transitory memory devices of the remote computing unit stores further instructions for controlling the one or more second processors to:
determine, based on the received particle data and the second particle data, whether the particle data is offset from the second particle data by a first offset.

35. The system of claim 33, wherein:
the monitoring unit is a mobile monitoring unit configured to be moved within the environment, and
the second monitoring unit is a stationary monitory unit in a fixed position within the environment.

36. The system of claim 33, wherein the monitoring unit and the second monitoring unit are mobile monitoring units configured to be moved within the environment.

37. The system of claim 33, wherein the one or more second non-transitory memory devices of the remote computing unit stores further instructions for controlling the one or more second processors to:
determine, based on the received particle data and the second particle data, whether the first exposure threshold has been exceeded for the monitoring unit.

38. The system of claim 29, wherein the first exposure threshold comprises a time-weighted average, an acute exposure limit, an upper exposure limit, a lower exposure limit, a combustible limit, and a short-term exposure limit.

39. The system of claim 29, wherein:
the monitoring unit further comprises an accelerometer, a gyroscope, and a microphone,
the one or more first non-transitory memory devices stores further instructions for controlling the one or more first processors to:
cause the accelerometer to generate accelerometer data, the gyroscope to generate gyroscopic data, and the microphone to generate sound data, and
transmit, using the first communications unit, the accelerometer data, gyroscopic data, and sound data, to the remote computing unit, and
the one or more second non-transitory memory devices stores further instructions for controlling the one or more second processors to determine, based on the accelerometer data, gyroscopic data, and sound data, an activity being performed within a first distance from the monitoring unit.

40. The system of claim 39, wherein the one or more second non-transitory memory devices stores further instructions for controlling the one or more second processors to determine, based on the accelerometer data, gyroscopic data, and sound data, whether a wearer of the monitoring unit is performing an activity.

41. A system comprising:
a monitoring unit positioned within an environment and that includes:
an air quality sensor configured to generate particle data regarding particles in the environment,
a first communications unit with an antenna configured to transmit data between the monitoring unit and, directly or indirectly, a remote computing unit, and between the monitoring unit and the second monitoring unit, and
a controller comprising one or more first processors and one or more first non-transitory memory devices that store instructions for controlling the one or more first processors to:
cause the air quality sensor to generate particle data about particles in the environment, and
transmit, using the first communications unit, the particle data generated by the air quality sensor to the remote computing unit;
a second monitoring unit positioned within the environment and that includes:
a second air quality sensor configured to generate data regarding particles in the environment,
a third communications unit with an antenna configured to transmit data between the second monitoring unit and the remote computing unit, and
a second controller comprising one or more third processors and one or more third non-transitory memory devices that store instructions for controlling the one or more third processors to:
cause the second air quality sensor to generate second particle data about particles in the environment, and transmit, using the third communications unit, the second particle data generated by the air quality sensor to the remote computing unit; and the remote computing unit positioned outside the environment and containing one or more second processors, one or more second communications unit, and one or more second non-transitory memory devices that stores instructions for controlling the one or more second processors to:

receive and store the particle data, receive and store the second particle data, determine, based on the received particle data generated by the air quality sensor, whether a first exposure threshold has been exceeded for the monitoring unit, and determine, based on the received second particle data, whether the first exposure threshold has been exceeded for the second monitoring unit.

42. The system of claim 41, wherein the first communications unit and controller are configured as a single unit.

43. The system of claim 41, further comprising a notification mechanism configured to present a person with a notification related to the particle data, wherein:

the one or more second non-transitory memory devices of the remote computing unit stores further instructions for controlling the one or more second processors to cause, based on the particle data, the notification mechanism to present the person with the notification related to the particle data.

44. The system of claim 41, wherein:

the one or more second non-transitory memory devices of the remote computing unit further stores environmental data about the environment, and the one or more second non-transitory memory devices of the remote computing unit stores further instructions for controlling the one or more second processors to:

access the environmental data, determine, based on the received particle data and the environmental data, second adjusted particle information, and determine, based on the second adjusted particle information, whether the first exposure threshold has been exceeded, wherein the environmental data comprises one or more of: material safety data sheet (MSDS) data, weather data, historical detected particle data, data generated by another monitoring unit in the environment, data regarding activity being performed in the environment, and public data.

45. The system of claim 41, wherein the one or more second non-transitory memory devices of the remote computing unit stores further instructions for controlling the one or more second processors to:

determine, based on the received particle data and the second particle data, whether the particle data is offset from the second particle data by a first offset.

46. The system of claim 41, wherein:

the monitoring unit is a mobile monitoring unit configured to be moved within the environment, and the second monitoring unit is a stationary monitory unit in a fixed position within the environment.

47. The system of claim 41, wherein the monitoring unit and the second monitoring unit are mobile monitoring units configured to be moved within the environment.

48. The system of claim 41, wherein the one or more second non-transitory memory devices of the remote computing unit stores further instructions for controlling the one or more second processors to:

determine, based on the received particle data and the second particle data, whether the first exposure threshold has been exceeded for the monitoring unit.

49. The system of claim 41, wherein the first exposure threshold comprises a time-weighted average, an acute exposure limit, an upper exposure limit, a lower exposure limit, a combustible limit, and a short-term exposure limit.

50. The system of claim 41, wherein:

the monitoring unit further comprises an accelerometer, a gyroscope, and a microphone, the one or more first non-transitory memory devices stores further instructions for controlling the one or more first processors to:

cause the accelerometer to generate accelerometer data, the gyroscope to generate gyroscopic data, and the microphone to generate sound data, and transmit, using the first communications unit, the accelerometer data, gyroscopic data, and sound data, to the remote computing unit, and the one or more second non-transitory memory devices stores further instructions for controlling the one or more second processors to determine, based on the accelerometer data, gyroscopic data, and sound data, an activity being performed within a first distance from the monitoring unit.

51. The system of claim 50, wherein the one or more second non-transitory memory devices stores further instructions for controlling the one or more second processors to determine, based on the accelerometer data, gyroscopic data, and sound data, whether a wearer of the monitoring unit is performing an activity.

52. A system comprising:

a monitoring unit positioned within an environment and that includes:

an air quality sensor configured to generate particle data regarding particles in the environment, an accelerometer, a gyroscope, a microphone, a first communications unit with an antenna configured to transmit data between the monitoring unit and, directly or indirectly, a remote computing unit, and a controller comprising one or more first processors and one or more first non-transitory memory devices that store instructions for controlling the one or more first processors to:

cause the air quality sensor to generate particle data about particles in the environment, cause the accelerometer to generate accelerometer data, cause the gyroscope to generate gyroscopic data, cause the microphone to generate sound data, transmit, using the first communications unit, the particle data generated by the air quality sensor to the remote computing unit, and transmit, using the first communications unit, the accelerometer data, gyroscopic data, and sound data, to the remote computing unit; and the remote computing unit positioned outside the environment and containing one or more second processors, one or more second communications unit, and one or more second non-transitory memory devices that stores instructions for controlling the one or more second processors to:

receive and store the particle data,
determine, based on the received particle data generated by the air quality sensor, whether a first exposure threshold has been exceeded for the monitoring unit, and
determine, based on the accelerometer data, gyroscopic data, and sound data, an activity being performed within a first distance from the monitoring unit.

53. The system of claim 52, wherein the first communications unit and controller are configured as a single unit.

54. The system of claim 52, further comprising a notification mechanism configured to present a person with a notification related to the particle data, wherein:
the one or more second non-transitory memory devices of the remote computing unit stores further instructions for controlling the one or more second processors to cause, based on the particle data, the notification mechanism to present the person with the notification related to the particle data.

55. The system of claim 52, wherein:
the one or more second non-transitory memory devices of the remote computing unit further stores environmental data about the environment, and
the one or more second non-transitory memory devices of the remote computing unit stores further instructions for controlling the one or more second processors to:
access the environmental data,
determine, based on the received particle data and the environmental data, second adjusted particle information, and
determine, based on the second adjusted particle information, whether the first exposure threshold has been exceeded, wherein the environmental data comprises one or more of: material safety data sheet (MSDS) data, weather data, historical detected particle data, data generated by another monitoring unit in the environment, data regarding activity being performed in the environment, and public data.

56. The system of claim 52, further comprising:
a second monitoring unit positioned within the environment and that includes:
a second air quality sensor configured to generate data regarding particles in the environment,
a third communications unit with an antenna configured to transmit data between the second monitoring unit and the remote computing unit, and
a second controller comprising one or more third processors and one or more third non-transitory memory devices that store instructions for controlling the one or more third processors to:
cause the second air quality sensor to generate second particle data about particles in the environment, and
transmit, using the third communications unit, the second particle data generated by the air quality sensor to the remote computing unit,
wherein:
the first communications unit is further configured to transmit data between the second monitoring unit, and
the one or more second non-transitory memory devices of the remote computing unit stores further instructions for controlling the one or more second processors to:

receive and store the second particle data,
determine, based on the received second particle data, whether the first exposure threshold has been exceeded for the second monitoring unit, and
determine, based on the received particle data and the second particle data, whether the particle data is offset from the second particle data by a first offset.

57. The system of claim 52, further comprising:
a second monitoring unit positioned within the environment and that includes:
a second air quality sensor configured to generate data regarding particles in the environment,
a third communications unit with an antenna configured to transmit data between the second monitoring unit and the remote computing unit, and
a second controller comprising one or more third processors and one or more third non-transitory memory devices that store instructions for controlling the one or more third processors to:
cause the second air quality sensor to generate second particle data about particles in the environment, and
transmit, using the third communications unit, the second particle data generated by the air quality sensor to the remote computing unit,
wherein:
the first communications unit is further configured to transmit data between the second monitoring unit, and
the one or more second non-transitory memory devices of the remote computing unit stores further instructions for controlling the one or more second processors to:
receive and store the second particle data, and determine, based on the received second particle data, whether the first exposure threshold has been exceeded for the second monitoring unit, wherein:
the monitoring unit is a mobile monitoring unit configured to be moved within the environment, and
the second monitoring unit is a stationary monitory unit in a fixed position within the environment.

58. The system of claim 52, further comprising:
a second monitoring unit positioned within the environment and that includes:
a second air quality sensor configured to generate data regarding particles in the environment,
a third communications unit with an antenna configured to transmit data between the second monitoring unit and the remote computing unit, and
a second controller comprising one or more third processors and one or more third non-transitory memory devices that store instructions for controlling the one or more third processors to:
cause the second air quality sensor to generate second particle data about particles in the environment, and
transmit, using the third communications unit, the second particle data generated by the air quality sensor to the remote computing unit,
wherein:
the first communications unit is further configured to transmit data between the second monitoring unit, and the one or more second non-transitory memory devices of the remote computing unit stores further instructions for controlling the one or more second processors to:
receive and store the second particle data, and
determine, based on the received second particle data, whether the first exposure threshold has been exceeded for the second monitoring unit, wherein the monitoring unit and the second monitoring unit are mobile monitoring units configured to be moved within the environment.

59. The system of claim 52, further comprising:
a second monitoring unit positioned within the environment and that includes:
a second air quality sensor configured to generate data regarding particles in the environment,
a third communications unit with an antenna configured to transmit data between the second monitoring unit and the remote computing unit, and
a second controller comprising one or more third processors and one or more third non-transitory memory devices that store instructions for controlling the one or more third processors to:
cause the second air quality sensor to generate second particle data about particles in the environment, and
transmit, using the third communications unit, the second particle data generated by the air quality sensor to the remote computing unit,
wherein:
the first communications unit is further configured to transmit data between the second monitoring unit, and
the one or more second non-transitory memory devices of the remote computing unit stores further instructions for controlling the one or more second processors to:
receive and store the second particle data,
determine, based on the received second particle data, whether the first exposure threshold has been exceeded for the second monitoring unit, and
determine, based on the received particle data and the second particle data, whether the first exposure threshold has been exceeded for the monitoring unit.

60. The system of claim 52, wherein the first exposure threshold comprises a time-weighted average, an acute exposure limit, an upper exposure limit, a lower exposure limit, a combustible limit, and a short-term exposure limit.

61. The system of claim 52, wherein the one or more second non-transitory memory devices stores further instructions for controlling the one or more second processors to determine, based on the accelerometer data, gyroscopic data, and sound data, whether a wearer of the monitoring unit is performing an activity.

62. A monitoring unit comprising:
a case with an inlet and an outlet;
an air quality sensor fluidically connected to the inlet and the outlet, and configured to generate particle data regarding particles in air drawn through the inlet;
a second air quality sensor fluidically connected to the inlet and the outlet, and configured to generate second particle data regarding particles in air drawn through the inlet;
a communications unit with an antenna configured to transmit data between the monitoring unit and a remote computing unit; and
a controller comprising one or more processors and one or more non-transitory memory devices, wherein:
the case encompasses the air quality sensor, the communications unit, and the controller, and
the one or more non-transitory memory devices store instructions for controlling the one or more processors to:
cause the air quality sensor to generate particle data about particles in air drawn through the inlet,
cause the second air quality sensor to generate second particle data about particles in air drawn through the inlet,
determine, based on the particle data and the second particle data, whether the particle data is offset from the second particle data by a first offset,
transmit, using the communications unit, the data generated by the air quality sensor to the remote computing unit, and
transmit information related to the determination of the first offset to the remote computing unit.

63. The monitoring unit of claim 62, further comprising a notification mechanism configured to present a person with a notification related to the particle data, wherein:
the one or more non-transitory memory devices stores further instructions for controlling the one or more processors to cause, based on the particle data, the notification mechanism to present the person with the notification related to the particle data.

64. The monitoring unit of claim 63, wherein the notification mechanism includes a display on the case that is configured to present the notification to the person.

65. The monitoring unit of claim 63, wherein the one or more non-transitory memory devices stores further instructions for controlling the one or more processors to:
receive a remote instruction from the remote computing unit, and
cause, based on the remote instruction received from the remote computing unit, the notification mechanism to present the person with the notification related to the particle data.

66. The monitoring unit of claim 63, wherein the notification is one or more of alarm, alert, message, an auditory output, an electronic communication, an electromagnetic communication, a visual output, and a tactile output.

67. The monitoring unit of claim 62, further comprising:
a temperature sensor;
a pressure sensor; and
a relative humidity sensor, wherein the one or more non-transitory memory devices stores further instructions for controlling the one or more processors to:
cause the air temperature sensor to generate temperature data,
cause the air pressure sensor to generate pressure data,
cause the relative humidity sensor to generate humidity data, and
transmit, using the communications unit, the temperature data, pressure data, and humidity data to the remote computing unit.

68. The monitoring unit of claim 62, wherein:
the communications unit is further configured to gather position data about a position of the monitoring unit within an environment, and
the one or more non-transitory memory devices stores further instructions for controlling the one or more processors to:

cause the communications unit is further configured to gather position data about the position of the monitoring unit within an environment, and transmit the position data to the remote computing unit.

69. The monitoring unit of claim 62, further comprising wearable features that are configured to enable the monitoring unit to be worn by a person within that person's breathing zone.

70. A monitoring unit comprising:

a case with an inlet and an outlet;

an air quality sensor fluidically connected to the inlet and the outlet, and configured to generate particle data regarding particles in air drawn through the inlet;

wearable features that are configured to enable the monitoring unit to be worn by a person within that person's breathing zone;

a communications unit with an antenna configured to transmit data between the monitoring unit and a remote computing unit; and a controller comprising one or more processors and one or more non-transitory memory devices, wherein:

the case encompasses the air quality sensor, the communications unit, and the controller, and the one or more non-transitory memory devices store instructions for controlling the one or more processors to:

cause the air quality sensor to generate particle data about particles in air drawn through the inlet, and transmit, using the communications unit, the data generated by the air quality sensor to the remote computing unit.

71. The monitoring unit of claim 70, further comprising a notification mechanism configured to present a person with a notification related to the particle data, wherein:

the one or more non-transitory memory devices stores further instructions for controlling the one or more processors to cause, based on the particle data, the notification mechanism to present the person with the notification related to the particle data.

72. The monitoring unit of claim 71, wherein the notification mechanism includes a display on the case that is configured to present the notification to the person.

73. The monitoring unit of claim 71, wherein the one or more non-transitory memory devices stores further instructions for controlling the one or more processors to:

receive a remote instruction from the remote computing unit, and cause, based on the remote instruction received from the remote computing unit, the notification mechanism to present the person with the notification related to the particle data.

74. The monitoring unit of claim 71, wherein the notification is one or more of alarm, alert, message, an auditory output, an electronic communication, an electromagnetic communication, a visual output, and a tactile output.

75. The monitoring unit of claim 70, further comprising:

a temperature sensor;

a pressure sensor; and a relative humidity sensor, wherein the one or more non-transitory memory devices stores further instructions for controlling the one or more processors to:

cause the air temperature sensor to generate temperature data, cause the air pressure sensor to generate pressure data, cause the relative humidity sensor to generate humidity data, and transmit, using the communications unit, the temperature data, pressure data, and humidity data to the remote computing unit.

76. The monitoring unit of claim 70, wherein:

the communications unit is further configured to gather position data about a position of the monitoring unit within an environment, and the one or more non-transitory memory devices stores further instructions for controlling the one or more processors to:

cause the communications unit is further configured to gather position data about the position of the monitoring unit within an environment, and transmit the position data to the remote computing unit.

* * * * *